(12) United States Patent
Diefenbach

(10) Patent No.: US 9,017,991 B2
(45) Date of Patent: Apr. 28, 2015

(54) METHODS TIP ASSEMBLIES AND KITS FOR INTRODUCING MATERIAL INTO CELLS

(75) Inventor: Thomas J. Diefenbach, Somerville, MA (US)

(73) Assignee: Tufts University, Boston, MA (US)

( * ) Notice: Subject to any disclaimer, the term of this patent is extended or adjusted under 35 U.S.C. 154(b) by 446 days.

(21) Appl. No.: 13/231,592

(22) Filed: Sep. 13, 2011

(65) Prior Publication Data

US 2012/0064518 A1 Mar. 15, 2012

Related U.S. Application Data

(63) Continuation-in-part of application No. PCT/US2010/027104, filed on Mar. 12, 2010.

(60) Provisional application No. 61/438,824, filed on Mar. 12, 2011, provisional application No. 61/159,856, filed on Mar. 13, 2009.

(51) Int. Cl.
*C12M 3/00* (2006.01)
*C12N 15/89* (2006.01)
*C12M 1/26* (2006.01)
*B01L 3/02* (2006.01)

(52) U.S. Cl.
CPC ............... *C12N 15/89* (2013.01); *C12M 33/04* (2013.01); *B01L 3/021* (2013.01)

(58) Field of Classification Search
CPC ......... C12N 15/89; C12M 33/04; B01L 3/021
USPC ................................ 435/285.1; 422/524, 525
See application file for complete search history.

(56) References Cited

U.S. PATENT DOCUMENTS

| | | | |
|---|---|---|---|
| 4,347,875 A * | 9/1982 | Columbus | 422/501 |
| 5,336,468 A | 8/1994 | Tezuka et al. | |
| 5,736,476 A | 4/1998 | Watzke et al. | |
| 5,922,687 A | 7/1999 | Mann et al. | |
| 6,117,394 A | 9/2000 | Smith | |
| 6,482,362 B1 | 11/2002 | Smith | |

(Continued)

FOREIGN PATENT DOCUMENTS

| | | |
|---|---|---|
| DE | 10361917 A1 | 7/2005 |
| DE | 102007004856 A1 | 8/2008 |

OTHER PUBLICATIONS

Beermann et al. 1994 Chapter 37: Chromophore-Assisted Laser Inactivation of Cellular Proteins Methods in Cell Biology, vol. 44, pp. 715-732.

(Continued)

*Primary Examiner* — William H Beisner
(74) *Attorney, Agent, or Firm* — Lawson & Weitzen LLP; Sonia K. Guterman; Michael I. Falkoff

(57) ABSTRACT

Methods, tip assemblies and kits are provided for introducing material into cells. The tip assemblies include an attachment portion, a channel portion, and a constriction that function to reduce fluid pressure as a fluid passes through the constriction portion from the channel portion, whereby the tip assemblies form pores in the membranes of cells and introduce material into the cells. The material includes for example one selected from the group of: an inorganic compound, a drug, a genetic material, a protein, a carbohydrate, a synthetic polymer, and a pharmaceutical composition.

7 Claims, 20 Drawing Sheets

(56) References Cited

U.S. PATENT DOCUMENTS

| | | |
|---|---|---|
| 6,596,240 B2 | 7/2003 | Taggart et al. |
| 6,982,063 B2 | 1/2006 | Hamel et al. |
| 7,318,911 B2 | 1/2008 | Smith |
| 7,341,966 B2 | 3/2008 | Marques |
| 7,794,664 B2 | 9/2010 | Pelletier et al. |

OTHER PUBLICATIONS

Buchstaller et al. Micro-scale chromophore-assisted laser inactivation of nerve growth cone proteins, "Microscop Res Tech," 2000, vol. 48, pp. 97-106.

Da Silva Bizario et al. "Expression of constructs of the neuronal isoform of myosin-va inteferes with the distribution of melanosomes and other vesicles in melanoma cells," Cell Motil Cytoskel, 2002, vol. 51, pp. 57-75.

Diefenbach et al. "Myosin 1c and myosin IIB serve opposing roles in lamllipodial dynamics of the neuronal growth cone," J Cell Biol, 2002, vol. 157, pp. 1207-1217.

Diefenbach et al. "Chapter 40: Chromophore-assisted laser inactivation of proteins by antibodies labeled with malachite green" in Cell Biology, 2006, 307-314.

Ericcson et al. "Identification of receptors for pig endogenous retrovirus" Proc Natl Acad Sci, 2003, vol. 100, pp. 6759-6764.

Espreafico et al. "Primary structure and cellular localization of chicken brain myosin-V (p190), an unconventional myosin with calmodulin light chain," J Cell Biol, 1992, vol. 119, pp. 1541-1557.

Shaner et al. "Improved monomeric red, orange and yellow fluorescent proteins derived from *Discosoma* sp. red fluorescent protein" Nat Biotech, 2004, vol. 22, pp. 1567-1572.

Svetina et al. "The cooperative role of membrane skeleton and bilayer in the mechanical behaviour of red blood cells" Bioelectrochem, 2004, vol. 62, pp. 107-113.

Tschoep et al. "Shock waves: a novel method for cytoplasmic delivery of antisense oligonucleotides" J Mol Med, 2001, vol. 79, pp. 306-313.

English abstract for DE 103 61 917 A (1 pg.).

English language abstract for DE 10 2007 004856 A1. DE 10 2007 004856 A1 is also published as WO2008/092607 (1 pg.).

Extended European Search Report in application No. 10 751 463.0 issued Sep. 17, 2013 by the European Patent Office (6 pgs.).

\* cited by examiner

500 μm

METHODS TIP ASSEMBLIES AND KITS FOR INTRODUCING MATERIAL INTO CELLS

RELATED APPLICATIONS

The present U.S. continuation-in-part utility application claims the benefit of U.S. provisional application Ser. No. 61/438,824 filed Feb. 2, 2011, and international application PCT/US2010/27104 filed Mar. 12, 2010 which claims the benefit of U.S. provisional application Ser. No. 61/159,856 filed Mar. 13, 2009, each of which is hereby incorporated herein by reference in its entirety.

TECHNICAL FIELD

Methods, tip assemblies and kits are provided for introducing material into cells. The material introduced into cells includes an inorganic compound, a drug, a genetic material, or a pharmaceutical composition.

BACKGROUND

Induced expression of genetic material, for example DNA sequences, in living cells is the foundation for molecular genetics and molecular biology. In this process, genetic material encoding for example for genes, is artificially introduced into the nucleus of a cell, so that the cell generates the product of the genes in the form of non-native or modified proteins, as is achieved by genetic engineering. In microbiology, the method by which one or more particular genes is altered in a recipient cell is referred to as transformation. In eukaryotic biology this method is sometimes referred to as transfection, or the introduction of a foreign cloned gene or cDNA into the eukaryotic genome. Viral or plasmid vectors are the vehicle for the introduction of DNA sequences.

Many methods have been employed to introduce genetic material into the nucleus or cytoplasm of living cells. These methods have limitations and require the conveyance of plasmid cDNA across plasma membranes, which are the heterogeneous bilayers of lipid molecules found on all cells. A well-known method to introduce genetic material into the nucleus or cytoplasm of living cells is electroporation, which relies on dielectric breakdown of the membrane producing gaps of up to 120 nanometers (nm) in diameter (metastable aqueous pores) in the membrane through which genetic material enters the cell through electrodiffusion. Another method is the use of transfection reagents including lipid or fat-based reagents (i.e., lipofectamine) which are essentially detergents that associate with DNA, thereby permitting the DNA to pass though the plasma membrane.

Biolistic transfection is yet another method, and involves a "gene gun" that fires the genetic material coupled to gold nanoparticles at high pressure through the plasma membrane. Mechanical injection is yet another method that typically uses glass needles that physically puncture the plasma membrane to deliver the genetic material using hydrostatic pressure injection directly into the nucleus.

Efficiencies of these methods have been found to have limitations, particularly due to toxicity, injury, or death to the cells. The transfection efficiency of such methods typically is very low or variable, depending upon the method and the cell type, and is related to the loss of viability of the treated cells, or the inability of the method to get the genetic material through the cell membrane. For example, transfection efficiency of the gene gun to treat a variety of different cell lines was observed to be successful with only about 1% to 4% of treated cells. Lipofection yields successful recombinants in only about 10% to 20% of treated cells. Polycationic lipid reagents generally do not exceed 40% efficiency. Most importantly, certain cell types are not amenable to any method, including certain types of immune system cells, human stem cells, muscle cells, nerve cells, and other cell types that do not divide and are therefore maintained in culture only as primary cells.

A more biological approach relies on virus-mediated transfection for introduction of genetic material into cells. This approach utilizes specific engineered viral vectors derived from strains such as adenovirus, sindbis virus, retrovirus, baculovirus or lentivirus, etc. to infect the cells. The viral genomes are engineered to carry the genetic sequences of interest, and are consequently a relatively time-consuming and labor-intensive method compared to mechanical means of introducing genetic material. This approach has a significant methodological limitation in that the time delay or lag to obtain protein expression depends not only on the efficiency of the cell to transcribe and translate the genetic material, but also on the infection efficiency of the virus. In addition, use of live virus requires special laboratory safety standard conditions, i.e., biohazard level 2.

Infection efficiency depends on many variables, and viral-mediated engineering is characterized by a lag of at least a day or several days to observe protein expression in cell populations. Furthermore, infection efficiency is cell-type specific, i.e., particular viruses do not infect certain cells.

There remains a need for a rapid, efficient, and universal method for introducing material such as genetic material into any type of cell, including cell types that have heretofore been difficult or impossible to transfect with any commercially available method.

SUMMARY

An aspect of the invention provides a tip assembly for introducing a composition in a fluid into cells, the assembly including: an attachment portion open to the atmosphere and proximally fitted to a flow device that generates at least one of a positive pressure and a negative pressure for impelling or directing the fluid; a channel portion contiguous to and distal to the attachment portion and the flow device; a constriction portion contiguous with the channel portion, such that a constriction portion inner diameter and a constriction portion cross sectional area respectively are smaller than a channel portion inner diameter and a channel portion cross sectional area respectively, and a distal end of the constriction portion has an opening for ejecting or drawing the fluid, such that increased fluid velocity and a decreased pressure in the fluid in the constriction portion compared to velocity and pressure in the channel portion enhances formation of membrane pores in the cells, so that the tip assembly introduces the composition into the cells through the membrane pores.

An embodiment of the tip assembly is disposable, alternatively, the tip assembly is reusable. In various embodiments, the tip is at least one selected from: translucent, transparent, modular, washable and sterilizable.

In various embodiments of the tip assembly, at least one of the attachment portion, the channel portion, and the constriction portion includes a substance selected from the group of: a glass, a metal, a plastic, a polymer, a nano-based composition, a composite material comprising at least two different types of substances, and the like. A nano-based composition includes: a nano-metal, a nano-ceramic, a nano-polymer, and the like. For example, tip assembly composed of the composite material is for example a glass and a polymer or a plastic and a polymer.

In an embodiment of the tip assembly, at least one of the attachment portion, the channel portion, and the constriction includes a surface component that prevents cell adherence, for example, a wax or a polymer.

The tip assembly in an embodiment has a distal end of the constriction that is non-lacerative, for example the distal end is diamond polished, heat-polished, chemically polished or flame-polished.

In an embodiment of the tip assembly, an inner diameter of the attachment portion of the tip assembly fits the flow device respectively, in a male to female arrangement. The tip assembly in an embodiment has an outer diameter of the attachment portion of the tip assembly respectively, that fits the flow device in a male to female arrangement, respectively. In an embodiment of the tip assembly, the attachment portion is smooth. Alternatively, the attachment portion includes a ridge, a protrusion or an indent. In various embodiments of the tip assembly, the attachment portion connects to a flow device by sliding, twisting, or rotating.

In various embodiments of the tip assembly, the attachment portion of the tip assembly that fits the flow device is selected from a pipette, a syringe, a compressor, or a pump. The compressor is a fluid compressor or an air compressor for impelling the fluid. In an embodiment of the tip assembly, and the pump includes a fluid pump or a pressure pump.

In embodiments of the tip assembly the channel portion cross sectional area or the constriction portion cross sectional area is bounded by a circle, an ellipse, a rectangle or a square. For example the channel portion is a rectangular channel and the constriction portion is a cylinder.

In an embodiment of the tip assembly, a distal end of the constriction portion has an inner diameter that is less than or substantially equal to an inner diameter of the opening. In various embodiments, the tip assembly includes or encompasses a volume selected from the group of about: 2 microliters (µl), 20 µl, 50 µl, 200 µl, 500 µl, 1 milliliter (ml), 5 ml, and about 10 ml. Greater volumes such as 50 ml, 100 ml and 500 ml are also envisioned as within the scope of the invention. In various embodiments, the channel portion inner diameter is about 1.0 millimeter (mm) to about 10.0 mm, and the dimension of the constriction inner diameter is about 0.05 mm to about 2.0 mm, such that the constriction inner diameter is smaller than the channel portion inner diameter.

In an embodiment of the tip assembly, the channel portion curvature and constriction inner curvature characterize a fluid path for the fluid flowing through the tip assembly which includes a formula. For example, the formula represented in two dimensions is $$f(x)=p1x^7+p2x^6+p3x^5+p4x^4+p5x^3+p6x^2+p7x+p8$$

wherein x is a radial distance from a center axis on the fluid path to an inner surface of the tip and coefficients with 95% confidence bounds in parentheses include: p1 is $-2.611e^{-16}$ ($-6.043e^{-16}$, $8.206e^{-17}$), p2 is $3.954^{e-13}$ ($-3.195^{e-13}$, $1.11^{e-12}$), p3 is $-1.845^{e-10}$ ($-7.821^{e-10}$, $4.131^{e-10}$), p4 is $1.662^{e-08}$ ($-2.394^{e-07}$, $2.726^{e-07}$), p5 is $7.537^{e-06}$ ($-5.186^{e-05}$, $6.694^{e-05}$), p6 is $-0.002137$ ($-0.009375$, $0.005101$), p7 is $-0.003185$ ($-0.4114$, $0.4051$), and p8=268.6 (261, 276.3). Alternatively, the formula represented in two dimensions is $$f(x)=p1x^8+p2x^7+p3x^6+p4x^5+p5x^4+p6x^3+p7x^2+p8x+p9$$

such that coefficients with 95% confidence bounds in parentheses include: p1 is 2.285 (1.388, 3.182), p2 is 3.465 (1.782, 5.149), p3 is $-15.68$ ($-20.04$, $-11.32$); p4 is $-20.38$ ($-27.24$, $-13.52$); p5 is 44.27 (36.5, 52.04); p6 is 53.96 (45.69, 62.23); p7 is $-58.72$ ($-64.02$, $-53.42$), p8 is $-123.5$ ($-126.4$, $-120.6$), and p9 is 186.5 (185.6, 187.4). The formula is various embodiments includes a formula in two dimensions that is substantially similar to formula $f(x)=p1x^7+p2x^6+p3x^5+p4x^4+p5x^3+p6x^2+p7x+p8$ and formula $f(x)=p1x^8+p2x^7+p3x^6+p4x^5p5x^4+p6x^3+p7x^2+p8x+p9$. For example the formula graphed on two dimensions lies between the two formulae above and results in the tip assembly functionally introducing the composition in a fluid into a cell the same as the formulae.

In an embodiment, the tip assembly curvature has a shoulder extending laterally from an outward surface of the attachment portion, for example the shoulder functions in manually removing the tip assembly from the flow device, or a lower ejector section of the flow device removes the tip assembly from the flow device programmably or manually. For example the shoulder includes a geometry selected from the group including: a cylinder, a cone, a rectangular, a regular polygon and a square.

The channel portion of the tip assembly has a length that is a function of the volume of fluid, or is a function of a peak velocity of fluid necessary for forming the pores in the cells. The channel portion generally has a marking or a plurality of markings for visually identifying or measuring the volume in the tip assembly.

An aspect of the invention provides a method for introducing a composition in a fluid into cells, the method involving: contacting the cells in a reservoir with a fluid including the composition; inserting a tip assembly into the reservoir, the tip assembly including: an attachment portion open to the atmosphere and proximally fitted to a flow device that generates at least one of a positive pressure and a negative pressure for directing the fluid; a channel portion contiguous to and distal to the attachment portion and the flow device; a constriction portion contiguous with the channel portion, such that a constriction portion inner diameter and a constriction portion cross sectional area are smaller than a channel portion inner diameter and a channel portion cross sectional area, a distal end of the constriction portion having an opening for ejecting or drawing the fluid, such that increased fluid velocity and a decreased pressure in the fluid in the constriction portion compared to velocity and pressure in the channel portion enhances formation of membrane pores in the cells; and, passaging a mixture of the cells, the fluid and the composition at least once through the tip assembly using a flow device that generates at least one of a positive pressure and a negative pressure, so that passaging the mixture forms the membrane pores in the cells and introduces the composition into the cells.

The cells passaged in the tip assembly are prokaryotic cells or are eukaryotic cells.

In various embodiments, the composition is at least one selected from the group of an inorganic compound, a drug, a genetic material, a protein, a carbohydrate, a synthetic polymer, and a pharmaceutical composition. For example the pharmaceutical composition is at least one agent selected from: an anti-tumor, an antiviral, an antibacterial, an antimycobacterial, an anti-fungal, an anti-proliferative and an anti-apoptotic. For example, the composition is a vector carrying a nucleic acid that encodes a protein or peptide having an amino acid sequence.

In various embodiments, the method further includes after passaging, observing localization of the composition to at least one subcellular compartment or cellular structure of a cell selected from: a nucleus, a mitochondrion, a Golgi body, a chloroplast, a chromoplast, an axon, a cytoplasmic membrane, a nuclear membrane, an endosome, a vesicle, a vacuole and a cytoplasm. For example the method in various embodiments further includes after passaging, observing localization of the composition to the nucleus of the cells, or observing localization of the composition to cytoplasm of the cells.

In an embodiment of the method, observing the localization further includes visualizing the composition with a detectable marker, for example the detectable marker is selected from the group consisting of: detectable, fluorescent, colorimetric, enzymatic, radioactive, and the like. For example, the detectable marker is a green fluorescent protein or a cyanine 3 fluorescent dye.

In various embodiments of the method, observing the localization further includes quantifying directly the product of the composition that entered the cell from the group consisting of mRNA, siRNA, shRNA, microRNA, DNA, RNA, and protein.

In an embodiment of the method, passaging the mixture further includes redirecting the mixture at least once to the reservoir. In an embodiment of the method, passaging the mixture further involves dispensing the mixture into a receptacle, or into one or more of a plurality of receptacles. In an embodiment of the method, passaging the mixture further involves dispensing the mixture into a constricted channel continuous with the constriction at the distal end of the tip.

In an embodiment of the method, the cells that are a population are a plurality of cells. The cells in general are living cells, and the method further involves measuring cell viability and observing that the cell viability is not substantially reduced. In various embodiments of the method the cell viability is at least about: 1%, 10%, 20%, 30%, 40%, 50%, 60%, 70%, 75%, 80%, 85%, 90%, or 95% of control cells not so contacted and/or passaged through the tip assembly. For example cell viability is determined by at least one method such as contacting the cells with propidium iodide, observing cell morphology using a microscope, and measuring cell attachment by resistance or impedance by measuring real-time cell electronic sensing (RT-CES) in a multi-cell culture dish or E-plate.

In an embodiment of the invention, passaging the mixture in the tip assembly reduces the pressure at the constriction portion at least about 0.05%, 1%, 5%, 10%, 10%, 20%, 30%, 40%, 50%, 60%, 70%, 75%, 80%, 85%, 90%, or 95% in contrast to the mixture passaged through the channel portion only.

In various embodiments of the method, prior to contacting, the method further includes preparing the fluid. For example, the fluid includes a $Ca^{+2}$ concentration less than about 500 nanomolar (nM), about 200 nanomolar (nM), about 150 nM, about 100 nM, about 75 nM, or less than about 50 nM. In various embodiments of the methods, the fluid includes a $Mg^{+2}$ concentration of at least about 0.5 millimolar (mM), at least about 1 mM, at least about 2 mM, at least about 5 mM or at least about 10 mM. In various embodiments of the method, the fluid includes a magnesium concentration of less than about 200 nanomolar (nM), about 150 nM, about 100 nM, or about 75 nM.

An embodiment of the method further includes after passaging, centrifuging the mixture to obtain a cell pellet and a supernatant. For example, the method further includes removing the supernatant, adding cell culture medium to the reservoir, re-suspending the cell pellet in the medium and culturing the cells.

An embodiment of the method uses cells that are living postmitotic cells. In various embodiments of the method, the cells include at least one cell type selected from the group consisting of: epithelial cells, hematopoietic cells, stem cells, spleen cells, kidney cells, pancreas cells, liver cells, neuron cells, glial cells, smooth or striated muscle cells, sperm cells, heart cells, lung cells, ocular cells, bone marrow cells, fetal cord blood cells, progenitor cells, tumor cells, peripheral blood mononuclear cells, leukocyte cells, and lymphocyte cells. In an embodiment of the method, the cells include physiologically inactive cells, for example the physiologically inactive cells are selected from the group of: inhibited, UV-inactivated, enucleated, anucleate, and heat-killed. In an embodiment of the method, the cells include non-reproducing cells or synthetic cells having an artificial membrane.

The method in various embodiments involves the composition that is a genetic material including a DNA or an RNA. In various embodiments of the method, the RNA is at least one selected from the group of: mRNA, tRNA, rRNA, siRNA, RNAi, miRNA, and dsRNA or a portion thereof. In an embodiment of the method, the DNA includes cDNA. In an embodiment, the method further includes observing transfection or transformation of the cells.

The method in various embodiments further includes applying to the mixture at least one selected from the group of: an electric field, a light comprising at least one wavelength, and a sound pulse. For example, the electric field, the light, or the sound pulse is used to further stabilize the cells in the mixture, activate the composition, or to further enhance the size or duration of the membrane pores in the cells for introducing the composition into the cells.

In various embodiments of the method, passaging is performed over a period of time, for example at least about 1 second, about 2 seconds, about 4 seconds, about 6 seconds, about 8 seconds, about 10 seconds, about 30 seconds, about 1 minute, about 3 minutes, about 5 minutes, about 10 minutes, about 15 minutes, about 20 minutes, or about 30 minutes. For example, the passaging is performed continuously over a period of time. Alternatively, the passaging is performed intermittently such that the period of time includes a plurality of passaging and also a plurality interruptions or pauses. For example, the period of passaging and/or the period of pauses is milliseconds. In various embodiments, the plurality of passaging and the plurality of pauses is about 2, about 5, about 10, about 15, about 20, about 25, about 30, about 40, about 50, about 75, and about 100 seconds.

An aspect of the invention provides a kit for introducing a composition in a fluid into cells the kit having a tip assembly for passaging a mixture of the cells and the fluid including: an attachment portion open to the atmosphere and proximally fitted to a flow device that generates at least one of a positive pressure and a negative pressure for impelling the fluid; a channel portion contiguous to and distal to the attachment portion and the flow device; a constriction portion contiguous with the channel portion, such that a constriction portion inner diameter and a constriction portion cross sectional area are smaller than a channel portion inner diameter and a channel portion cross sectional area, such that a distal end of the constriction portion comprises an opening for ejecting or drawing the fluid, such that increased fluid velocity and a decreased pressure in the fluid in the constriction portion compared to velocity and pressure in the channel portion enhances formation of membrane pores in the cells, whereby the tip assembly introduces the composition into the cells through the membrane pores; and a container.

In an embodiment, the kit further includes a reservoir or a receptacle. In an embodiment, the kit further includes instructions for use, for example, at least one instruction including: contacting the cells in a reservoir with the fluid including the composition; inserting the tip assembly into the reservoir; contacting the attachment portion of the tip assembly to a flow device that generates at least one of a positive pressure and a negative pressure; and passaging a mixture of the fluid and the composition at least once through the tip assembly using the flow device, whereby passaging the mixture forms the membrane pores in the cells and introduces the composition into the cells. In an embodiment of the kit, the instructions include methods for obtaining or directing fluid into the reservoir or the receptacle.

The kit in various embodiments further includes one or more of a transfection agent, a buffer, or a medium for at least one cell, cell line, or cell strain. In an embodiment, the kit further includes a flow device that applies at least one of a positive pressure and a negative pressure for directing or impelling the fluid.

An aspect of the invention provides a system for introducing composition in a fluid into cells, the system having a flow device that generates at least one of a positive pressure and a negative pressure for impelling the fluid; and, a tip assembly for passaging a mixture of the cells and the fluid including: an attachment portion that connects to the flow device, a channel portion contiguous to and distal to the attachment portion and the flow device, a constriction portion contiguous with the channel portion, such that a constriction portion inner diameter and a constriction portion cross sectional area are smaller than a channel portion inner diameter and a channel portion cross sectional area, such that a distal end of the constriction portion includes an opening for ejecting or drawing the fluid, such that increased fluid velocity and a decreased pressure in the fluid in the constriction portion compared to velocity and pressure in the channel portion enhances formation of membrane pores in the cells, whereby the system introduces the composition into the cells through the membrane pores.

The system in an embodiment further includes a receptacle adjacent to the opening for receiving or retaining the fluid passaged through the tip assembly. In an embodiment, the system further includes a plurality of receptacle (e.g., tubes, vials, flasks, beakers, and plates) adjacent to the opening for receiving or retaining the fluid passaged. The system in an embodiment further includes an optical device for detecting the cells and/or the composition, for example, a flow cytometer, a microscope, a mass spectrometer, a UV detector, a spectrophotometer, or a cell counter.

In various embodiments of the system, the tip assembly includes at least one selected from the group consisting of: a glass, a metal, a plastic, a polymer, a nano-based composition, a composite material that includes at least two different types of substances; and the like.

In an embodiment of the system, the distal end of the constriction portion is polished and smooth, for example the distal end is heat polished.

The flow device in various embodiments of the system includes at least one selected from the group of: a syringe, a plunger, a bulb, a diaphragm, and a compressor.

In an embodiment of the system, the flow device is controlled or operated manually. In various embodiments of the system, control and operation of the flow device is at least one selected from: automated, electromechanical, and programmable. For example the system further includes a computer or user interface that controls and operates the system. For example the computer is connected to the computer or user interface using wireless components or using a connector such as an electric cord or USB connector.

In various embodiments of the system, control and operation of the flow device includes the control of at least one selected from the group of: flow velocity; flow acceleration; mass flow rate; initial velocity ramp; starting velocity; maximum velocity; starting position; inflow velocity ramp, outflow velocity ramp, inflow velocity, outflow velocity, cutoff velocity; period of time the fluid is under pressure generated by the flow device; temperature, and period of time the fluid is held in the channel portion, constriction portion, or both.

In various embodiments of the system, the flow device generates a flow velocity along the length of the tip assembly, the flow velocity selected from about: about 0.1 centimeter per second to about 1 cm/s, about 1 cm/s to about 5 cm/s, about 5 cm/s to about 15 cm/s, about 15 cm/s to about 20 cm/s, and about 20 cm/s to about 40 cm/s.

In various embodiments of the system, the flow device generates a mass flow rate selected from a group consisting of about: 0.01 milliliter per minute (ml/min), 1 ml/min, 10 ml/min, 25 ml/min, 50 ml/min, 100 ml/min, and 150 ml/min.

In various embodiments of the system, the flow device generates a fluid acceleration in the tip assembly of about 0.6 microliters per second per second ($\mu$l/s/s), about 1 $\mu$l/s/s, about 6 $\mu$l/s/s, about 10 $\mu$l/s/s, about 12 $\mu$l/s/s, about 24 $\mu$l/s/s, about 36 $\mu$l/s/s, about 48 $\mu$l/s/s, and about 60 $\mu$l/s/s.

The tip assembly in an embodiment of the system further includes at least one valve. In various embodiments, the valve is situated or located proximal to or in the channel portion, between the channel portion and the constriction portion, in the constriction portion, distal or adjacent to the constriction portion, or adjacent to the opening. For example, the valve is used to introduce at least one of the fluid, the composition or the cells. In an embodiment of the system, the at least one valve includes a plurality of valves, for example positioned adjacent to the opening or proximal to the constriction portion.

The system in various embodiments is a closed system with the opening being connected to the valve for example using a conduit, thus for re-circulating the mixture or the fluid from the opening to the channel portion, or for directing the mixture or the fluid from the channel portion to a receptacle.

The system in an embodiment further includes a power source, for example a battery, power cell, or solar panel.

In an embodiment, the system further includes a connector for interacting with at least one of: a user interface, a computer, a hand-held device, a transmitter, and a display. For example, the transmitter connects to a server which then connects to a computer.

The system in an embodiment includes a conduit for connecting the flow device to the tip assembly. For example the connector includes tubing for example plastic or polymer tubing. In an embodiment of the system, the tubing includes at least one filter or membrane for the cells.

In an embodiment the system is located in a housing. For example the housing is located primarily on a bench or table, or alternatively is mobile. In an embodiment, the housing is located on or within a high-throughput sampling or testing device.

The system in an embodiment includes a sensor for sensing the flow device or the fluid. In various embodiments of the system, the sensor detects at least one selected from the group of: pressure, time, temperature, flow device signal, flow device current, and flow device location. In embodiments of the system, the sensor communicates with the flow device or a microprocessor.

In an embodiment of the system, the flow device directs iterations of passaging the fluid and the cells through the tip assembly. In various embodiments of the system, the cells include or are at least one cell type selected from the group consisting of: epithelial cells, hematopoietic cells, stem cells, spleen cells, kidney cells, pancreas cells, liver cells, heart cells, lung cells, ocular cells, sperm cells, smooth or striated muscle cells, glial cells, neuronal cells, bone marrow cells, fetal cord blood cells, premitotic cells, progenitor cells, peripheral blood mononuclear cells, leukocyte cells, and lymphocyte cells.

In various embodiments of the system, the composition is at least one selected from the group of: an inorganic compound, a drug, a genetic material, a protein, a carbohydrate, a synthetic polymer, and a pharmaceutical composition. For example, the genetic material includes DNA or RNA.

BRIEF DESCRIPTION OF THE DRAWINGS

FIG. 1 panel A is a drawing of a three-dimensional representation of an inner surface of an exemplary tip assembly having a top or proximal opening which is located proximal to source of the material, fluid, and pressure, and a bottom or distal opening which is distal to the source of material, fluid, and pressure. The drawing shows that the tip assembly has a channel portion of a greater inner diameter and cross-section area than a distally located constriction portion. Changes in the radial dimension are not shown to scale relative to the proximal-distal dimension to emphasize the geometry of the distal end of the tip assembly. The scale bar is 200 micrometers (microns; μm).

FIG. 1 panel B is a curve showing the relationship between the length of the tip along the fluid path from the proximal to the distal opening and a radial distance from a center axis on the fluid path to an inner surface of the tip assembly, fitted using the eighth degree polynomial function characterizing the curvature of the tip assembly shown in FIG. 1 panel A. The radial distance of the inner surface of the tip assembly from a center axis on the fluid path (microns) is shown on the ordinate and the length of the tip along the fluid path (microns) is shown on the abscissa. The fluid path along the inner surface of the tip from the proximal (top) opening channel portion and constriction to the distal (bottom) opening is shown from left to right.

FIG. 1 panel C is a photograph of an exemplary tip of a tip assembly for introducing material in a fluid in a cell, with a smaller tip diameter (175-200 μm), and a constriction portion of length 250 μm proximal to the distal opening of the tip assembly. The tip assembly was made from custom fabricated glass tube having an ID of 0.88 mm, OD of 1.23 mm and wall thickness of 0.14 mm.

FIG. 1 panel D is a drawing of a three-dimensional representation of an exemplary tip as shown in FIG. 1 panel C. The drawing shows that the tip opening is narrower than the opening of the tip shown in FIG. 1 panel A. The drawing also shows a constriction portion, 250 μm long proximal to the distal end of the tip assembly. Scale bar is 500 μm.

FIG. 2 panel A is a drawing of a three-dimensional representation of the inner surface an exemplary tip assembly having a top or proximal opening which is located proximal to source of the material, fluid, and pressure, and a bottom or distal opening which is distal to the source of material, fluid, and pressure. The drawing shows that the tip assembly has a channel portion of a greater inner diameter and cross-section area than a distally located constriction portion. Changes in the radial dimension are not shown to scale relative to the proximal-distal dimension to emphasize the geometry of the distal end of the tip assembly. The scale bar is 200 micrometers μm.

FIG. 2 panel B is a curve showing the relationship between the length of the tip along the fluid path from the proximal to the distal opening and the radial distance from a center axis on the fluid path to the inner surface of the tip, fitted using the eighth degree polynomial function characterizing the curvature of the tip assembly shown in FIG. 2 panel A. The radial distance of the inner surface of the tip assembly from a center axis on the fluid path (μm) is shown on the ordinate and the length of the tip along the fluid path (μm) is shown on the abscissa. The fluid path along the inner surface of the tip from the proximal (top) opening channel portion and constriction to the distal (bottom) opening is shown from left to right.

FIG. 4 panel B is a set of photographs each showing a ciliary ganglion neuronal cell that is the recipient of genes encoding GFP, introduced by the methods and devices herein. The photograph on the top is a brightfield microscope field of view, and the photograph on the bottom is a fluorescence microscope field of view. These data show that GFP expression is maximal at 48 hours after receiving the GFP gene. Further, GFP expression is abundant in compartments in the cytoplasm and absent from the nucleus.

FIG. 5 panel B is a set of photographs each showing the same ciliary ganglion neuron from the same culture as shown in FIG. 3 panel A, photographed at 28 hours after the genetic material was introduced into the cell. The photograph on the left is a brightfield microscope field of view, and the photograph on the right is an epifluorescence microscope field of view, each taken at the same point in time. These photographs show localization of myosin Va to each of the cell body and the neuronal processes, particularly the branch points (b) and the tips of the growing axonal processes (indicated in the immunofluorescent photographs by asterisks).

FIG. 6 panel A is a set of fluorescence image photomicrographs taken with a laser scanning confocal microscope (LSCM) of neuronal growth cones transfected with constructs carrying a gene (myosin-Va GFP, myosin-Va tail GFP and GFP control). Each of a construct encoding an enhanced GFP-fusion protein encoding the full-length (FL) neuronal isoform of chicken myosin-Va heavy chain, and a construct encoding a truncated form consisting of the full tail (FT) region that includes the entire IQ motif, were transfected into neurons using a method described herein. Growth cones of cells transfected with the construct carrying the gene encoding myosin-Va GFP showed increased abundance of enhanced GFP myosin-Va in the central and peripheral growth cone regions and along neuronal projections compared to cells transfected with the construct carrying the gene encoding myosin-Va mutant tail region or a control GFP construct control. These data demonstrate successful transfection of neuronal cells with the two different myosin Va protein-encoding constructs, and also a role of myosin-Va in filopodial length extension. Scale bar is 10 µm.

FIG. 6 panel B is a set of brightfield DIC micrographs of individual growth cones transfected with a construct carrying a gene encoding myosin-Va. GFP, a construct carrying a gene encoding myosin-Va tail GFP, or a construct carrying a gene encoding the GFP control. Growth cones transfected with the gene encoding myosin-Va GFP were observed to display significantly longer finger-like membrane projections (filopodia) than growth cones transfected with the control gene encoding GFP. Growth cones tranfected with the construct carrying the gene encoding the mutant tail region of myosin-Va showed significantly shorter filopodia compared to growth cones transfected with the gene encoding GFP or the gene encoding myosin-Va GFP. Data from these photomicrographs demonstrate that successful transfection was observed, and that transfection of the different myosin Va protein variants resulted in specific and different effects in growth of nerve cell projections at the growing tips. Scale bar is 10 µm.

FIG. 6 panel C is a set of bar graphs showing filopodial length of growth cones observed at each of eight hours (left) and 15 hours (right) after transfection and plating. Enhanced GFP-myosin-Va overexpression was observed to result in significantly increased average filopodial length at eight hours and 15 hours post-transfection ($p<0.01$, Student's t-test).

FIG. 8 panel A shows HUVEC cells transfected using a tip assembly with vectors carrying genes encoding a fusion protein of enhanced green fluorescent protein (EGFP) and HuPAR2. The left photograph shows the cell visualized by differential interference contrast (DIC); the middle photograph shows the same cell visualized by a fluorescence microscope; and the right photograph shows an overlay of the DIC photograph and the fluorescence microscope photograph. Data show that the tip assembly effectively transfected the cell as determined by intense staining observed in perinuclear subcellular compartments indicating presence of the EGFP-HuPAR2 fusion protein in the cell. Scale bar is 10 µm.

FIG. 8 panel B is a photomicrograph of several HUVEC cells transfected using a tip assembly with vectors carrying genes encoding the fusion protein of EGFP and HuPAR2. The cells were visualized by DIC. The photomicrograph shows significant perinuclear staining of GFP-HuPAR2 protein in HUVEC cells. The DIC data for these plurality of HUVEC cells transfected with genes that encode a fusion protein of EGFP and HuPAR2 are substantially similar to DIC data in the photograph of the single transfected HUVEC cell (FIG. 8 panel A, left photograph).

FIG. 10 panel A is a photograph of a computer programmable syringe pump 101, 102 connected to an external computer by means of a USB converter 103 and an RS232 interface 104 configured in the inner side of the metal lid 105 of a jump box 106. The RS232 interface 104 to USB converter 103 connection is linked by a cable to an external computer for control using the data analysis software MATLAB (Mathworks, Natick, Mass.).

FIG. 10 panel B is an enlarged view of the programmable syringe 101 and the pump mechanism 102 positioned on the jump box 106 right. The exemplary syringe 101 is borosilicate glass, has a UHMWPE (ultra-high molecular weight polyethylene) seal 107 which lubricates and is solvent resistant, and has a plunger 108. A length of TYGON® tubing 109 connected at one end to the syringe is routed through the metal lid 105 of the jump box 106 to a connector, and to tubing that attaches directly to the proximal end of a soda lime glass capillary tube.

FIG. 10 panel C shows a power supply 110 located inside the jump box 106 to the lower left.

FIG. 10 panel D is a photograph of the jump box 106 inside a tissue culture flow hood for sterile conditions. The metal lid 105 is in the closed position, and the outer lid 111 is in an open position. The TYGON® tube 109 for connecting to a tip extends from the metal lid 105, to the edge 112 of the metal lid 105.

FIG. 12 panel A shows EGFP-CDC42 staining observed 24 hours after transfection using laser scanning confocal microscopy. The staining was observed in the cytoplasm at the periphery compared to little or no staining in the nucleus of the cell.

FIG. 12 panel B shows EGFP-CDC42 expression as a result of transfection in a pair of daughter cells that had recently divided. Expression was observed to be concentrated in a region between daughter cells.

FIG. 12 panel C shows a larger magnification of HUVEC cells transfected with EGFP-CDC42 at standard PMT (photomultiplier tube) sensitivity. Fluorescence was observed localized to large granules.

FIG. 12 panel D shows HUVEC cells transfected with EGFP-CDC42 in which the image was scanned at a higher than standard PMT sensitivity. EGFP-CDC42 expression was observed in subcellular granules smaller in size than granules observed in panel C.

FIG. 13 panel A shows a cluster of primary HUVEC cells transfected with EGFP-actin. Transfection and expression of EGFP was observed localized to actin filaments of the cell cytoskeleton.

FIG. 13 panel B is an image of a primary HUVEC cells transfected with EGFP-actin showing expression of EGFP in the actin filaments of the cell.

FIG. 13 panel C is a bar graph showing EGFP-actin mRNA copy number in HUVEC cells transfected with the methods and devices herein or with an AMAXA Nucleofactor™ (Lonza Cologne GmbH, Cologne, Germany) electroporation unit. TC indicates transfection with the plasmid and CT indicates a control procedure absent the EGFP-actin plasmid. AMAXA indicates data obtained with the AMAXA Nucleofactor™ electroporation unit.

FIG. 15 panel A is a confocal fluorescence microscope image of a few primary mouse brain astrocytes transfected with EGFP plasmid. The cell with a round shape has fluorescence intensity near background level.

FIG. 15 panel B is a confocal fluorescence microscope image of a cluster of primary mouse brain astrocytes transfected with EGFP plasmid showing cells with varying levels of fluorescence intensities.

FIG. 15 panel C is a confocal fluorescence microscope image of a group of primary mouse brain astrocytes transfected with EGFP plasmid showing a cell with high fluorescence intensity surrounded by cells with lower levels of fluorescence intensities.

FIG. 15 panel D is an overlay of a confocal fluorescence microscope image of a primary mouse brain astrocyte transfected with EGFP plasmid on a brightfield image of the same cell, showing morphological features of the cell.

FIG. 15 panel E is a confocal fluorescence microscope image of two primary mouse brain astrocytes transfected with Cy3-labeled miRNA showing internalized miRNA, which is localized mostly in the cytoplasm as tiny round spots.

FIG. 15 panel F is a confocal fluorescence microscope image of a group of mouse brain astrocytes transfected with Cy3-labeled miRNA showing varying levels of internalization of miRNA in different cells. The Cy3-labeled miRNA is excluded from the nucleus.

DETAILED DESCRIPTION OF EMBODIMENTS

Figure 1A:
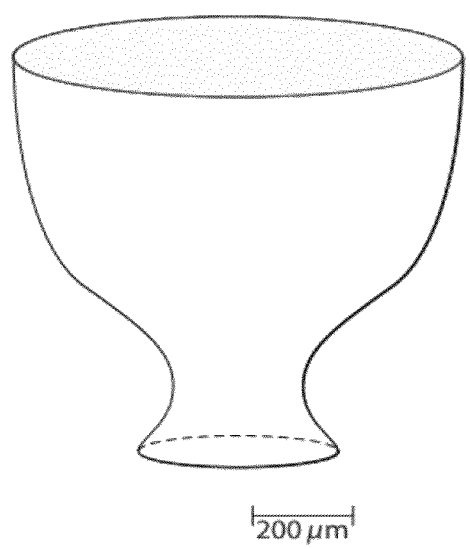
FIG. 1 is a drawing and graph showing an exemplary shape of the interior surface of a tip assembly for introducing a material such as a composition in a fluid into a cell.
Figure 1B:
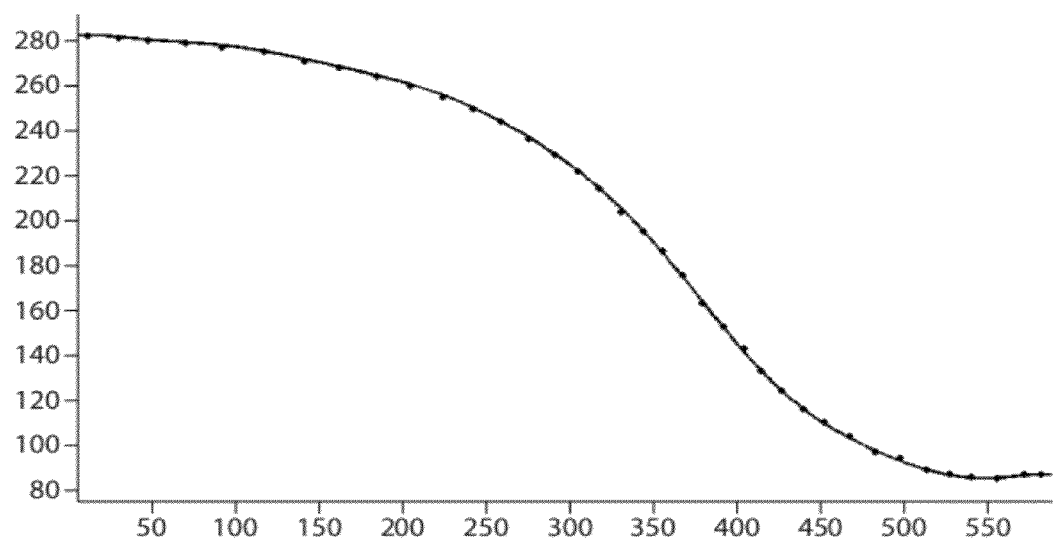
Figure 1C:
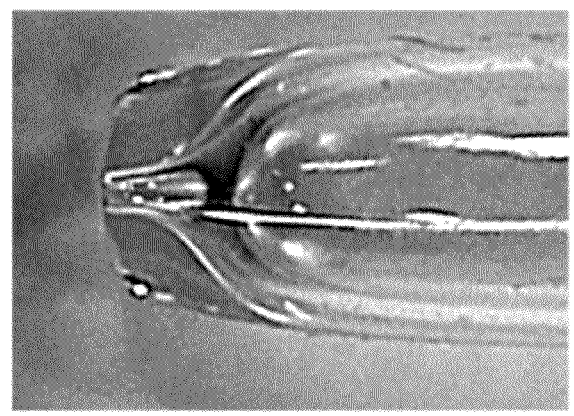
Figure 1D:
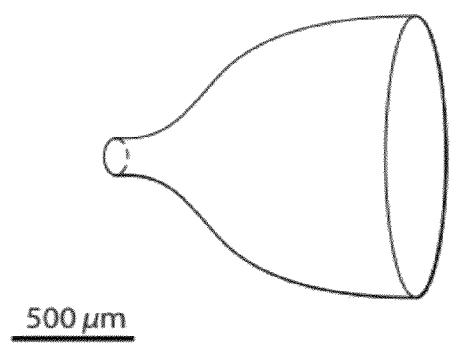

The invention herein provides methods, devices and kits for introducing material into cells, for example for introducing a composition such as a genetic material into living cells or non-viable cells. The methods, devices and kits herein utilize high fluid velocities, and the examples herein show that cell survival during the loading process is enhanced, resulting in reliable and highly efficient expression of recombinant proteins in cultured transfected cells.

Cells are surrounded by a plasma membrane comprising a bilayer of lipids and fat molecules. The integrity of the plasma membrane is affected by the electrostatic forces among the individual lipid molecules, and by interactions between the membrane and the underlying cellular cytoskeleton. Individual lipid molecules diffuse through the plane of inner leaflets and outer leaflets of the bilayer. The behavior of these lipid molecules within the bilayer is described using the fluid mosaic model of the plasma membrane that states that the lipid bilayer is charged and polar to both repel water and prevent the passage of water into and out of the cell. The bilayer serves as a barrier also for biological molecules including nucleic acids, proteins, and fats.

Without being limited by any particular theory or mechanism of action, the methods herein using fluid dynamic technology, in combination with low $Ca^{+2}$ conditions, passaging cells at such high velocity that plasma and possibly also nuclear membranes are stretched momentarily, thereby producing transient holes in the membranes that permit entry of plasmid or linear DNA in a molecular shape that is long and relatively thin. As the diameter of a single DNA helix is 2 nanometer (nm), and as circular DNA plasmid is subject to coiling and supercoiling, the plasmid acquires a structural configuration capable of entering a cell through resulting openings in the cell membrane produced by the methods as described herein. Electroporation results in openings as great as 120 nm in diameter, in certain examples herein it is envisioned that the methods herein result in openings in the membrane similar to this size, for example about 60 nm to about 100 nm, about 100 nm to about 120 nm, or about 120 to about 140 nm.

The term "cells" includes living cells, non-metabolizing, resting or inhibited cells, and non-reproducing cells. For methods herein, cells are suspended in a fluid or medium in a container, and a pressure differential is applied across the plasma membrane. The pressure differential is caused inter alia by different pressures exerted by the ionic constituents of the medium, the cytoplasm, and pressure exerted on the medium. Compressibility of the medium is a factor that affects the pressure differential. Cells are conveniently placed in various types of media, generally in aqueous media which includes biological and naturally occurring fluids such as blood or tissue. Water is relatively incompressible, and compressibility is not related to observed pressure differences imposed on the cell in aqueous media. Water temperature if constant does not affect the fluid density, which also remains constant. This pressure of an incompressible fluid is termed static pressure.

Molecules in a fluid are in constant state of motion and exert pressure on the walls of a container, which is referred to as total pressure. If set into directed or ordered motion, a dynamic pressure is produced which is an additional type of pressure associated with momentum of moving molecules. Therefore motion of molecules contributes to static pressure, i.e., dynamic pressure. The addition of dynamic pressure to the static pressure results in a total pressure in a flowing system. Thus, a cell in a fluid is subject to a number of dynamic forces and pressures.

Additional fluid dynamics factors are considered in the circumstances of fluid passing in a conduit or tube into a narrowed or constricted portion. The change in pressure accompanying a change in fluid velocity through a tube with a changing cross section area is described by the Bernoulli equation which states that if a fluid flowed through a reduction in cross-sectional area of a tube an accompanying reduction in pressure and an increase in fluid velocity would be observed. The Bernoulli equation states $$v^2/2 + gz + p/r = \text{constant}$$

in which v is the fluid flow speed at a point in the streamline, g is the acceleration due to gravity, z is elevation to a point above a reference plane with a z direction opposite to the direction of gravitational acceleration, p is the pressure, and r is the fluid density. Bernoulli's principle elucidates a reduction in tube diameter resulting in a decrease in fluid pressure, a process known as the Venturi effect.

The Venturi effect occurs as a result of satisfaction of the law of conservation of energy, from a fluid passing through a constriction increasing the fluid velocity in the constriction to conserve mass. As the velocity of the fluid increases so does the kinetic energy. Therefore a decrease in fluid pressure occurs to counteract the increase in kinetic energy.

Cells moving in a fluid-filled channel or passageway undergo an increase in speed in a constriction of the channel, in passing through a narrower diameter exit aperture. These cells in suspension experience a sudden change from high pressure to low pressure. Low pressure results in temporary stretching of the cells, creating temporary holes in cell membranes, permitting entry of material present in the fluid or solution surrounding the cells, including without limitation genetic materials cDNA, siRNA, miRNA. Low $Ca^{+2}$ concentration in the fluid or solution promotes prolongation of time required for cell membrane sealing, further promoting entry of material down a pressure and concentration gradient through the holes in the membrane and into the cell interior. The Bernoulli principle is a mechanism by which fluid pressure facilitates entry of large molecules such as DNA, or other molecules in the fluid such as smaller molecules including a drug into the cells.

Examples herein utilize a tip assembly that includes a channel portion and a constriction to create pores or holes in a cellular membrane. An exemplary three dimensional representation of the tip assembly shape is shown in FIG. 1 panel A. Without being limited by any particular theory or mechanism of action, it is envisioned that after passage of cells through the narrowing or constriction as shown for example in FIG. 1 there is a distal opening with curved edges for two-way passaging, in one embodiment an enlargement into a more distal continuation of the channel into a section having the same, larger or smaller diameter. The inside curvature of the shape shown in FIG. 1 panel A is represented in two dimensions as a cross section (FIG. 1 panel B). The cross sections of the tip assembly are parallel to the fluid flow. An exemplary curvature of the fluid flow and tip assembly shape in one embodiment characterized in two dimensions by the following equation:

$$f(x) = p1x^8 + p2x^7 p3x^6 + p4x^5 + p5x^4 + p6x^3 p7x^2 + p8x + p9$$

where x is a radial distance from a center axis on the fluid path to an inner surface of the tip, and the coefficients (with 95% confidence bounds in parentheses) are: p1 is 2.285 (1.388, 3.182); p2 is 3.465 (1.782, 5.149); p3 is −15.68 (−20.04, −11.32); p4 is −20.38 (−27.24, −13.52); p5 is 44.27 (36.5, 52.04); p6 is 53.96 (45.69, 62.23); p7 is −58.72 (−64.02, −53.42), p8 is −123.5 (−126.4, −120.6); and p9 is 186.5 (185.6, 187.4). Parameters applied to obtain goodness of fits were: sum of squares due to error (SSE) is 66.5, r-square ($R^2$) is 0.9997, adjusted $R^2$ is 0.9997, and root mean squared error (RMSE) 1.341.

Figure 2A:
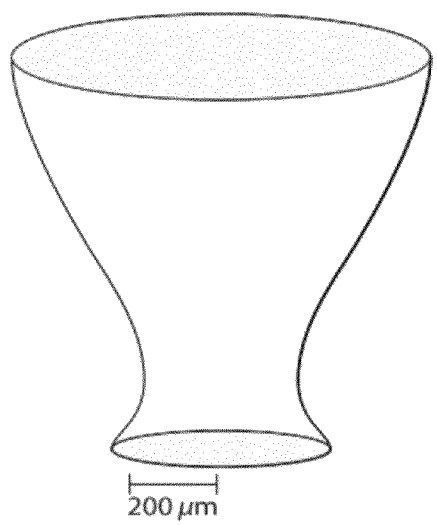
FIG. 2 is a drawing and graph showing an exemplary shape of a tip assembly for introducing material in a fluid into a cell.
Figure 2B:
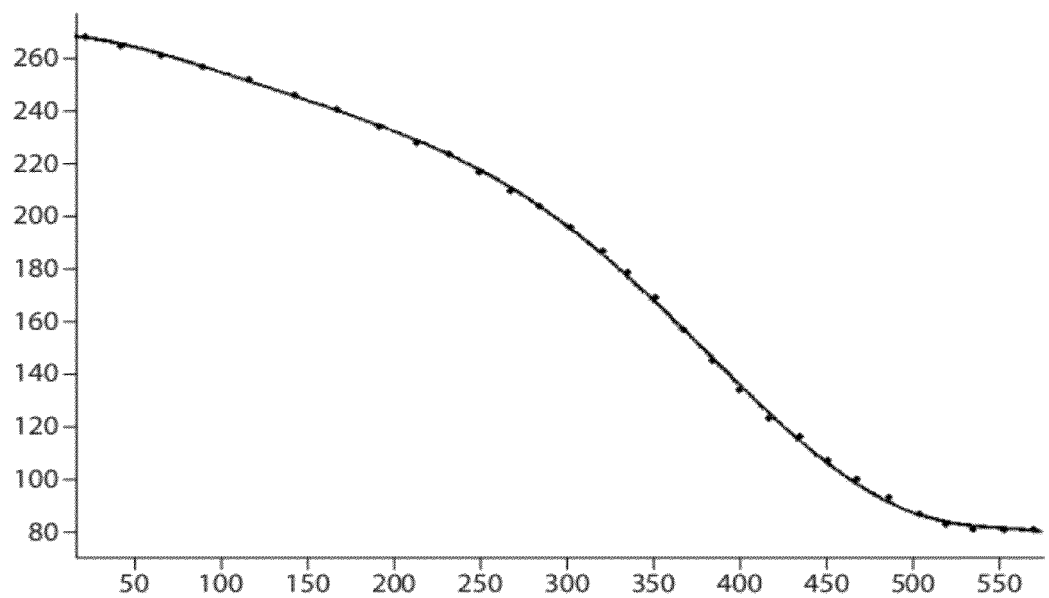

The skilled artisan alters the degree of change in curvature in the tip assembly to change the rate at which the pressure changes during fluid flow. For example, the various channel portions are constructed having various lengths depending on a necessary volume of fluid, fluid pressure, or fluid velocity for introducing material into cells. For example, a 2 centimeter (cm) channel portion having a 1 millimeter (mm) inner diameter at the proximal end is constructed to sufficiently accelerate 50 µl of fluid through the tip assembly. Thus, curvature is made steeper or shallower than the embodiment of curvature shown in FIG. 1 panels A and B. A shallower curvature is shown in three dimensions in FIG. 2 panel A. The cross-sectional shape of the inside curvature of the fluid path in two dimensions is shown in FIG. 2 panel B. This two dimensional curve is fitted using the eighth degree polynomial equation denoted and which is shown below:

$$f(x)=p1x^7+p2x^6+p3x^5+p4x^4+p5x^3+p6x^2+p7x+p8$$

where x is a radial distance from a center axis on the fluid path to an inner surface of the tip, and the coefficients (with 95% confidence bounds in parentheses) are: p1 is $-2.611e^{16}$ ($-6.043e^{-16}$, $8.206e^{-17}$); p2 is $3.954^{e-13}$ ($-3.195^{e-13}$, $1.11^{e-12}$); p3 is $-1.845^{e-10}$ ($-7.821^{e-10}$, $4.131^{e-10}$); p4 is $1.662^{e-08}$ ($-2.394^{e-07}$, $2.726^{e-07}$); p5 is $7.537^{e-06}$ ($-5.186^{e-05}$, $6.694^{e-05}$); p6 is $-0.002137$ ($-0.009375$, $0.005101$); p7 is $-0.003185$ ($-0.4114$, $0.4051$); and p8=268.6 (261, 276.3). Parameters used to obtain goodness of fit were: SSE is 31.09, $R^2$ is 0.9998, adjusted $R^2$ is 0.9997, and RMSE is 1.189.

Without being limited by any particular theory or mechanism of action, changes in curvature in the tip assembly are customized for the characteristics of the fluid used (e.g., viscosity, temperature, and molecular components) and also on the type of cell utilized as larger cells may required larger constriction sizes. Blood cells for example are only about 5 μm to about 10 μm in diameter. In contrast, *Xenopus laevis* oocytes are 1000 μm or 1 mm in diameter. Cells having a larger surface area to volume ratio (i.e., smaller cells) generally would be used in methods herein with smaller diameter constrictions and greater pressure reductions. For example a suitable pressure reduction in the tip assemblies herein includes at least about 0.1%, about 0.5%, 1%, 5%, 10%, 15%, 20%, 25%, 30%, 35%, 40%, 45%, 50%, 55%, 60%, 70%, 75%, 80%, 85%, 90%, or about 95%. The pressure drop resulting from the reduction in diameter of the path leading to the distal opening is dependent on volumetric flow rate and the change in diameter. For example, given a gradual reduction in diameter from 1 mm to 0.25 mm, with a flow rate of 5 ml/min of water, the pressure drop would be 0.28 millibar (mbar); with a flow rate of 10 ml/min, the pressure drop would be 5.55 mbar; with a flow rate of 10 ml/min, the pressure drop would be 5.55 mbar; with a flow rate of 50 ml/min, the pressure drop would be 27.9 mbar; with a flow rate of 100 ml/min, the pressure drop would be 55.6 mbar; and with a flow rate of 150 ml/min, the pressure drop would be 2643.4 mbar. The tip assemblies herein are used for any cell type including smaller or larger cells including animal cells, plant cells, and prokaryotic cells.

The extent of reduction in diameter of a fluid path determines the decrease in fluid pressure. The manner and degree to which the fluid pressure decreases affects the rate and amount of pore formation in the cellular membrane for a cell moving in the fluid path. FIG. 1 panel A and FIG. 2 panel A show an exemplary fluid path and channel shape that narrows and accordingly decreases the fluid pressure and enhances pore formation in cells in the fluid path. The channel located proximal to the constriction has a uniform non-varying shape that leads to the distal narrowing or constriction. The tip assemblies envisioned herein have fluid paths or curvatures that are exemplified by the formulas above.

The tip assemblies are manufactured in various embodiments of any of a variety of suitable materials and suitable aperture sizes. The tip in related embodiments is manufactured of a polymer such as a water repellent material or coated with an agent to prevent cell adhesion to the tip assembly or droplet formation that prevents accurate dispensing of the fluid.

Methods for constructing tips include blow molding, vacuum forming, and thermoforming, are described in Smith, U.S. Pat. Nos. 7,318,911; 6,482,362; and 6,117,394 issued Jan. 15, 2008, Nov. 19, 2002, and Sep. 12, 2000; Pelletier et al., U.S. Pat. No. 7,794,664 issued Sep. 14, 2010; Taggart et al., U.S. Pat. No. 6,596,240 issued Jul. 22, 2003; and Tezuka et al., U.S. Pat. No. 5,336,468 issued Aug. 9, 1994. Borosilicate glass materials and methods are shown for example in Marques, U.S. Pat. No. 7,341,966 issued Mar. 11, 2008 and Watzke et al., U.S. Pat. No. 5,736,476 issued Apr. 7, 1998.

The methods and tip assemblies are suitable for incorporation into automated robotic systems, for reliable introduction of DNA into cells in a rapid and high-throughput manner. For example, the tip assemblies herein are used to transfect and to transduce cells in an automated manner to reduce contamination of cells. The tip assemblies herein are envisioned in various embodiments as attaching to manual pipettes and to automated pipettes and dispensing systems such as single-tip pipette systems and multi-tip pipette systems respectively.

Without further limiting the invention, it is here envisioned that one or more alternative mechanisms may operate to produce the observed transfection effects. Unlike most existing approaches that rely upon shock, pH, high energy or ultrasonics to affect the energetic of pore transport, these other hypothesized mechanisms rely on cell deformation per se rather than deformation arising from the cell flowing through a narrowing channel.

Repeated exposure of a cell in fluid suspension to distortion in a way that the shape of the cell alternates between spherical and oblate may cause rearrangement of the cortical cytoskeleton underlying the plasma membrane, affecting mobility of lipids or lipid rafts, which can influence membrane pore formation. The fluidity of the membrane may be affected by changes in the underlying cytoskeleton (in a manner similar to that noted in red blood cells by Sventina et. al., 2004, Bioelectrochemistry, 62: 107-113; and gross cellular deformation (such as flattening of the cell) may contribute to changes in fluidity. A pressure change that might expose the cells to repeated compression/expansion independent of fluid flow (ie: a static suspension) may potentially also lead to pore formation, since pore formation itself will be dependent upon membrane fluidity. Such repetition at a rate substantially lower than existing sonic or ultrasonic frequencies, may also be visualized as resulting in a peristalsis of the cell or low-frequency pulsing that may affect the barrier energy that prevails at a pore under static cellular conditions. To optimize this effect for particular cells and transfection agents, the extent of such effects may be tested, quantified or otherwise established using a different test instrument to introduce a sudden pressure change or sequence of changes within a static fluid column. This flow-free mechanism would be relatively free of potentially destructive shear conditions which have been known to damage cells in prior art transfection protocols.

The cultured neurons transfected by methods and devices shown in examples herein include postmitotic cells that have reached a final developmental stage and do not further divide. Neurons are fragile, and prior art manipulation techniques, such as electroporation, have been found to damage the cells such that regeneration capabilities for physiological processes and viability in culture are negatively impacted.

Primary cultures of certain neurons such as ciliary ganglion neurons and dorsal root ganglion neurons, have typically been used at a stage that is optimal for experimental manipulation, from one hour to twelve hours after culturing. Beyond twelve hours after culturing, the neuronal processes become so intertwined and overgrown that even in low density cultures the ability to monitor neuronal regeneration and outgrowth becomes increasingly limited with time. Thus, a method to rapidly introduce and express genetic material in cells such as neurons remains a long-felt need. It is envisioned that cell-based experimental systems that require rapid expression of genes will benefit from the methods and tip assemblies described herein. Furthermore, high-throughput transfection required in such processes as protein production can be improved using the rapid and efficient nature of this method and apparatus. Another application of this method is found in cell-based gene therapy for clinical use, for example, gene silencing using siRNA.

The methods herein for introducing a composition such as a genetic material into cells provide significant improvements over the prior art because the method is rapid, reliable, economical (with no need for expensive reagents); recipient cells are characterized by very high viability and expression efficiency. Using the prior art method of electroporation, the highest efficacy obtained is only about 40% of recipient cells which express the nucleic acid. For adenovirus infection expression the highest efficacy obtained is about 30% to 85% and is generally lower. Gene guns typically achieve between 1% and 5% efficiency.

In contrast, the methods herein resulted in visible protein expression in neurons (postmitotitic cells) within three hours post-transfection. In addition, the present method achieved consistently high transfection efficiencies of 80% to about 100% within 24 hours.

Furthermore, the methods herein advantageously do not require viruses, for example, recombinant adenoviruses, which require biosafety level 2 due to infectiousness. The present method is performed without use of toxic chemicals, complex procedures, or viruses. Cells that are dissociated from tissues or from the surface of a culture plate are suitable materials for use in the methods herein. Therefore methods herein are applicable to cells of a tissue obtained by dissociation, and to cells suspensions e.g., primary cells and cultured cells of a cell line.

The methods herein are applicable also to a tissue in situ, and to a monolayer of cells in culture. The methods herein bypass the relatively lengthy periods of time (several hours or days) required for chemical or viral vectors to express genes for functional analysis. Certain methods such as cationic reagents, the gene gun, and electroporation are limited by the size or length of cDNA that can be used, thereby limiting the types of proteins which can be addressed in an experiment or screen. Examples herein include use of a very large plasmid encoding the full-length protein of myosin Va, which has a molecular weight of about 110 kDa. The data in the Examples herein show that constructs of different sizes, for example DNA encoding proteins that are much larger than myosin Va, were introduced into cells more effectively and efficiently using the method, tip assembly and kits of the present application than by conventional methods. Introducing the genetic material in Examples herein also includes using a transfection agent or a plurality of transfection agents. For example, the transfection agent is a nanoparticle, a liposome, a viral vector, a bacteriophage, and a detergent. For example, the transfection agent is Lipofectamine.

An exemplary method includes one passage, or a plurality of passages, for example about five to ten passages, that are performed within a one minute period. For example, a single passage or multiple passages, repeated passages performed at more than one time, are rapidly performed. Depending on the cell type, additional embodiments are envisioned to include passaging five times every ten minutes for a specific period of time, for example, during a time period of about one hour, about two hours, or about five hours.

In general, it was observed that a plurality of passages was consistently sufficient to introduce material, e.g., genetic material and a drug, into a plurality of cells. Cells were maintained in cell culture medium at a suitable temperature, e.g., 37° C., after a single treatment, or between treatments.

The term "introducing" as used herein refers to any of a variety of methods for delivering a composition such as a macromolecular or a low molecular weight molecule into a cell, either in vitro or in vivo, such methods including transformation, transduction, transfection, and infection. Vectors include plasmid vectors and viral vectors. Viral vectors include retroviral vectors, lentiviral vectors, or other vectors such as adenoviral vectors or adeno-associated vectors. Methods for constructing vectors are shown for example in Ericsson, T. A. et al. 2003 PNAS vol. 100 (10): 6759-6764.

The term "passaging", as used herein means impelling a composition or a mixture, for example a solution or a suspension, through at least a portion of a length of the apparatus and tip assembly, i.e., a proximal portion, a middle portion, and a distal portion. In related embodiments, passaging means impelling the fluid entirely through the apparatus, including removing a suspension of cells from a receptacle into the pipe portion and replacing the cells into the same receptacle, or distributing the cells through the tip assembly portion into a plurality of receptacles, or into at least one of the plurality of receptacles.

The methods herein were performed on different cell types, some of which have previously been categorized as refractory to genetic manipulation. Cell types include for example immortalized cells, actively growing cells, for example, cells in culture, and also postmitotic cells for example isolated as primary cultures. Examples herein demonstrate successful use of the methods with cells that have not in the past conveniently responded favorably to transfection reagents or to electroporation, resulting in low viability, or cell-type specific differences in transfection efficiency. Further, expression of protein encoded by the introduced genetic material using the methods herein was observed to be significantly more rapid, within three hours of the treatment, which is at least about a two to three fold faster rate of expression of genes compared to the rate observed following introduction of genes by prior art methods.

The myosin-Va constructs described in Examples herein are derived from the chicken neuronal isoform of myosin-Va (Espreafico E. M., et al., 1992 J. Cell Biol. 119(6): 1541-1557). A construct pCB6-FL (EGFP-MVa with FL referring to full length) contains the myosin-Va full length heavy chain (amino acid residues 1-1830) in a pCB6 plasmid. A truncated form of MVa consists of the entire last IQ motif (from ARV to SRV, amino acid residues 880-1830) pEGFP-FT (EGFP-MVaFT, with FT referring to full tail). These constructs expressed in melanoma cells were shown to have effects on melanosome trafficking (da Silva Bizario J. C., et al., (2002) Cell Motil. Cytoskeleton 51(2): 57-75).

An aspect of the present invention provides a pressurized fluid flow apparatus including: a pipe portion having an inner diameter and an outer diameter and a distal end and a proximal end, such that the distal end is open to the atmosphere, such that the inner diameter of the pipe portion is about 1.0 mm to about 5.0 mm; the apparatus further including an exit tip assembly adjacent to and contiguous with the distal end of the pipe portion, such that the exit tip assembly has an inner diameter and an outer diameter, the inner diameter of the exit tip assembly being about 0.1 mm to about 0.5 mm; and a suction device connected to the proximal end of the pipe portion for generating positive pressure and negative pressure. The exit tip assembly is further optimized in Examples herein.

A related embodiment of the apparatus further includes a receptacle adjacent to the exit tip assembly for receiving and retaining fluid passaged through the pipe portion and exit tip assembly. An embodiment of the apparatus includes a pipe portion with a diameter that varies along the length of the pipe portion, for example, from a larger diameter to a smaller diameter to a larger diameter, the smaller diameter constituting a constriction of the pipe.

An embodiment of the pipe portion and/or the exit tip assembly includes at least one of from: borosilicate glass, aluminosilicate glass, and the like. In a related embodiment, the pipe and/or the tip includes flint glass (including lead oxide, titanium dioxide, zirconium dioxide or similar metals) and the like. Alternatively, the pipe and/or tip includes a plastic, such as a polymer.

An embodiment of the apparatus includes the distal end of the exit tip assembly polished by heat treatment to create a non-lacerative surface. For example, heat treatment includes flame-polishing. A non-lacerative surface of the distal exit opening or hole of the tip assembly minimizes shearing of cells when encountering the edge of the distal exit tip assembly at high velocities, thereby improving efficiency of the process by increasing viability of treated cells.

In general, the suction device generates a flow velocity along the length of the pipe portion, the velocity selected from at least one of a group consisting of about: 5 cm/s, 15 cm/s, and 20 cm/s. In an embodiment of the apparatus, the suction device generates a flow velocity along the length of the pipe portion, the flow velocity selected from at least one of about 5 cm/s to about 10 cm/s, about 10 cm/s to about 15 cm/s, about 15 cm/s to about 20 cm/s, and about 20 cm/s to about 40 cm/s.

In general, the suction device generates a mass flow rate at the distal exit of the tip assembly, the flow rate selected from at least one of about: 0.03 ml/min, 0.06 ml/min, 0.3 ml/min, 0.5 ml/min, 1.0 ml/min, and 2.0 ml/min. In an embodiment of the apparatus, the suction device generates a mass flow rate at the exit tip assembly selected from at least about: 0.01 ml/min, 0.05 ml/min, 0.1 ml/min, 0.2 ml/min, 0.4 ml/min, 0.8 ml/min, 1.2 ml/min, 1.5 ml/min, and about 3 ml/min.

A related embodiment of the apparatus includes the suction device that generates a mass flow rate along the length of the pipe portion selected from at least one of about: 1.0 ml/min, 5 ml/min, 10 ml/min, 50 ml/min, 100 ml/min, and 150 ml/min. For example, the suction apparatus generates a mass flow rate along the pipe portion selected from at least one of about 15 ml/min, at least about 25 ml/min, at least about 40 ml/min, at least about 60 ml/min, at least about 75 ml/min, at least about 90 ml/min, or at least about 125 ml/min.

An embodiment of the suction device is manually controlled. The phrase "manually controlled" as used herein means operated directly by the user, so that at least one of the choices of flow rates and access to cells and receptacles is controlled by the user at the time of use. In an alternative embodiment, the suction device is automated, i.e., is at least partially or completely controlled automatically so that the user need not even be present, for example the device is robotic and operationally linked to a computer program and computer. A related embodiment of the suction device includes at least one device that is manually controlled, and at least one device that is automated.

An embodiment of the distal exit opening having a tip assembly further includes a constriction in a continuous flow system controlled by at least one valve, for example, is controlled by two, three, or four valves, etc. For example, the at least one valve is a plurality of valves positioned laterally proximal to the distal exit hole, within millimeters or micrometers proximal to the exit, or all are proximal to the exit, for example, arrayed circularly around the exit. Alternatively, at least one or more of the plurality of valves is distal to the exit.

An aspect of the present invention provides a method for introducing a material such as a protein, a lipid, genetic material, or a drug or other low molecular weight component into a cell, the method including: contacting in a receptacle at least one cell with a composition including an effective amount of the material to obtain a resulting mixture; and, inserting the apparatus of any of the embodiments herein into the receptacle and passaging the mixture of cells and the material through the apparatus at least once, such that passaging the mixture having the cells and the material through the apparatus introduces the material into the cell. In general, a composition includes a fluid. For example, the fluid contains a solution or a suspension, for example of the material, the cells, and other components.

In an embodiment of the method, the cell is a prokaryotic cell. Alternatively, the cell is a eukaryotic cell.

In general, introducing genetic material results in localizing the genetic material to the nucleus of the cell. Alternatively, introducing the genetic material results in localizing the genetic material into the cytoplasmic or non-nuclear parts of the cell, for example, into the endoplasmic reticulum, Golgi apparatus, mitochrondrion, and/or lysosomes or other membrane bound compartments in the cytoplasm. In a related embodiment, the method after or during localizing further involves visualizing the genetic material in the nucleus or in the cytoplasm of the cell using a detectable marker. For example, the detectable marker is an agent that is at least one of fluorescent, colorimetric, enzymatic, radioactive, and the like.

An embodiment of the method includes after passaging the mixture through the apparatus, dispensing the mixture into the receptacle. Alternatively, the method includes after passaging the mixture through the apparatus, and dispensing the mixture into a plurality of receptacles. For examples, passaging further involves dispensing the mixture of the cell and the material at least once into the same receptacle, i.e., the receptacle that originally housed the cells. Alternatively, the method involves passaging the mixture through the apparatus, and dispensing the mixture into each of a first receptacle and a second receptacle. An embodiment of the method involving a large number of receptacles is envisioned as automatically controlled, for example, by robotics.

An embodiment of the method includes passaging the cell and the material in the apparatus at least once for a period of time selected from at least one of about: 0.1 minutes, 0.3 minutes, 0.5 minutes, 0.75 minutes, 1 minute, 1.5 minutes, 2.0 minutes, 5.0 minutes, 7.0 minutes, 10.0 minutes, 15.0 minutes, 20.0 minutes, and 30 minutes.

In various embodiments, the cell is a member of a population in a plurality of cells. In a related embodiment, the viability of the cells is not substantially reduced, i.e., the efficiency of plating of cells of the population remains substantially the same in comparison to control cells not passaged, or control cells passaged absent material.

An embodiment of passaging includes dispensing the mixture of cell and the material at least once into the receptacle, i.e., removing cells from the receptacle into the apparatus and distributing cells into the receptacle at least one once.

An embodiment of the receptacle is a centrifuge tube. An embodiment of the method includes passing or passaging the mixture of cells and genetic material through a constriction in a continuous pipe having an entry point and an exit point. Such a system is used herein, for example, in a flow-based, high throughput transfection system.

In various embodiments of the method, the fluid includes a $Ca^{+2}$ concentration that is less than about 200 nM. For example, the composition includes a $Ca^{+2}$ concentration that is less than about 150 nM, less than about 100 nM, or less than about 50 nM.

An embodiment of the fluid includes a $Mg^{+2}$ concentration that is at least about 1.5 mm. For example, the fluid includes a $Mg^{+2}$ concentration of at least about 3 mM, at least about 10 mm, at least about 20 mm, or at least about 50 mm.

In related embodiments, the method further includes, after passaging, centrifuging the mixture to obtain a cell pellet and supernatant. For example, the method further includes removing the supernatant, adding cell culture medium to the receptacle, and re-suspending the cell pellet in the medium. In a related embodiment, the method further includes culturing the cells.

In related embodiments of the method, the cells are living postmitotic cells. For example, the postmitotic cells are neurons or sperm cells. For example, the neurons are ciliary ganglion neurons or dorsal root ganglion neurons.

Alternatively, the cells are living premitotic cells. For example, the premitotic cells are at least one cell type selected from epithelial cells, hematopoietic cells, liver cells, and spleen cells.

In an embodiment of the method, the cells are physiologically inactive, such as inhibited by a chemical inhibitor, UV-inactivated, enucleated, anucleate, or heat-killed.

The material in some embodiments is a genetic material such as DNA or RNA. In a related embodiment, the DNA is cDNA. Alternatively, RNA is at least one selected from mRNA, tRNA, rRNA, siRNA, RNAi, miRNA, and dsRNA. In an embodiment of the method, the fluid includes at least one transfection agent. In related embodiments, the at least one transfection agent is selected from: a nanoparticle, a liposome, a viral vector, a bacteriophage, and a detergent. For example, the transfection agent is Lipofectamine.

An embodiment of the invention provides a kit for introducing a material into a nucleus of a living cell, the kit including the apparatus and/or tip assembly of any of the embodiments herein. In related embodiments, the kit further includes at least one of a receptacle, instructions for use, and a transfection agent. For example, the transfection agent is selected from: a nanoparticle, a liposome, a viral vector, a bacteriophage, and a detergent. For example, the transfection agent is Lipofectamine.

An embodiment of the invention provides a method for introducing a material into at least one cell in a tissue or a monolayer of cells in culture, the method including: inserting the apparatus of any of the embodiments described herein into a receptacle, such that the receptacle contains a composition including an effective amount of the material; and, contacting the at least one cell in the tissue or the monolayer in culture, such that contacting includes ejecting the composition under pressure onto the cell or cells, such that the material is introduced into the cell in the tissue or the cells of the monolayer. In related embodiments the material is a genetic material, a protein, or a drug.

In general, ejecting the composition under pressure includes generating a pressure wave having a particular frequency. The phrase "mechanical waves" refers to waves which propagate through a material medium (solid, liquid, or gas) at a wave speed that depends on elastic and inertial properties of that medium. Wave motions of mechanical waves include longitudinal waves and transverse waves. In general in the methods herein, the pressure wave is a longitudinal wave, and the particle displacement is parallel to the direction of wave propagation.

An embodiment of the method further includes, following contacting, observing the material entering the at least one cell without disrupting cell membranes or tissue. For example, observing includes analyzing cell membranes using a microscope. In an embodiment of the method, the cell is a prokaryotic cell. Alternatively, the cell is a eukaryotic cell.

In general, ejecting the cells from the apparatus results in localizing the material, e.g., the genetic material, to the nucleus of the cell. Alternatively, ejecting results in localizing the material to cytoplasmic parts of the cell for example, endoplasmic reticulum, Golgi apparatus, mitochrondrion, and lysosome.

An embodiment of the method includes visualizing the material with a detectable marker. In related embodiments, the detectable marker is an agent that is at least one of fluorescent, colorimetric, enzymatic, or radioactive. For example, the material if DNA encodes a fluorescent protein, or the material if a protein includes a fluorescent tag.

In general, the cell is a plurality of cells. In an embodiment of the method, the cell is a living cell within a population of living cells, and the viability of the cells is not substantially reduced.

In general, the genetic material is DNA or RNA. For example, the DNA is cDNA. For example, the RNA is at least one class of RNA selected from the group consisting of mRNA, tRNA, rRNA, siRNA, RNAi, miRNA, and dsRNA. The material in other embodiments is a protein or a polypeptide, such as insulin, EGF, EPO, or IGF II.

In general, the tissue is a mammalian tissue. For example, the mammalian tissue is a human tissue, for example, skin, kidney, pancreas, liver, lung, heart, brain, spinal cord, bone marrow, and eye. An embodiment of the monolayer includes stem cells, for example, at least one stem cell selected from hematopoietic, hemangioblast, mesenchymal, hepatocyte, pancreatic, pulmonary, neural, fetal, and embryonic. The tissue may also be derived from other vertebrate species including mouse, rat, pig, goat, horse, cow, monkey, fish and bird. Alternatively the method may also be used with living cells from invertebrate species including roundworm, molluscs, insects, echinoderms, and the like, or with living cells from plant cells or from yeast.

The invention having now been fully described, it is further illustrated by the following examples and claims, which are illustrative and are not meant to be further limiting. Those skilled in the art will recognize or be able to ascertain using no more than routine experimentation, numerous equivalents to the specific procedures described herein. Such equivalents are within the scope of the present invention and claims. The contents of all references, including issued patents and published patent applications cited throughout this application, are hereby incorporated herein by reference in their entireties.

EXAMPLES

Example 1

Deficiencies of Prior Art Techniques

Methods to load antibodies into neuron cells (trituration) have been attempted to reduce protein expression (Beerman et al., (1994) Methods Cell Biol 44: 715-732; Buchstaller et al., (2000) Microsc Res Tech 48(2): 97-106; Diefenbach et al., (2002) J Cell Biol 158(7): 1207-1217; Diefenbach et al., In: Celis J E, Carter N, Simons K, Small J V, Hunter T, Shotton D, editors. (2002) Cell Biology-A Laboratory Handbook. 3rd Edition (4 volumes). As antibody molecules are significantly smaller in molecular mass and overall length than are sequences of plasmid DNA, and as a DNA molecule would have to pass through not only the plasma membrane but also the inner nuclear membrane, these prior efforts have demonstrated the limitations of getting such larger macromolecules such as plasmid DNA into cells or into the nuclei of cells.

Trituration requires substantially higher velocities and changes in pressure for the significantly larger plasmid DNA to penetrate one or two membrane systems of the cell. Further, such higher velocities result in loss of membrane integrity, and indeed trituration loading at higher velocities causes substantial cell death, the creation of cellular debris from ruptured cells, introduction of air bubbles, and difficulties in suitable design and method.

Examples 2

Design of an Apparatus to Introduce Genetic Material into Living Cells

To produce a device to introduce a material into living cells, borosilicate glass tubes were precision flame-polished at one end (tip) to reduce the size of the opening to less than or about 0.2 to about 0.5 mm in diameter. Using this device, the cells were passed through a significantly smaller diameter passageway than has previously been used for cell passaging, with a result that the cell velocity significantly increased as the diameter of the passageway narrowed. The narrowing of the exit tip assembly of the glass tube generated the greater fluid velocities for introduction of the genetic material into the living cells. Most important, the cells necessarily had undergone a rapid change in fluid pressure as a result of the change in fluid velocity. The curvature of the inner surface of the narrowed portion of the fluid path contributed to the cell pore formation and cellular membrane openings. Further, the highly polished end was produced to prevent shear forces from forming as the cells encountered edges along the fluid path, therefore the polished end was observed to have enhanced cell viability.

Examples herein describe tip assemblies and methods of use for introducing material into a cell. FIG. 1 panel A and FIG. 2 panel B are three-dimensional representations of exemplary shapes of inner surfaces of tips having a top opening proximal to an apparatus that applies a pressure such as a pump which impels a fluid, a channel portion leading to a constriction portion, and a distal opening for releasing the fluid. The channel portion has a greater inner diameter and cross-section area than the constriction portion.

FIG. 1 panel B and FIG. 2 panel B are graphs of the eighth degree polynomial function used to describe a plot of the tip assemblies of FIG. 1 panel A and FIG. 2 panel B respectively.

The graphs describe a radial distance of the tip from a center axis of the fluid path on the ordinate, as a function of the length of the tip on the abscissa. The plot shows the fluid path along a length that includes: the inner surface of the tip from the proximal opening to the channel portion and constriction portion and to the distal opening.

Data in examples herein were obtained with neurons and non-neuronal cells using magnesium/calcium solutions generally having 1.5 mM $Mg^{+2}$/200 nM $Ca^{+2}$. A low $Ca^{+2}$ concentration in the solution was used to protect the cells from calcium-induced cell death, and prolong the open state of membrane holes or pores. Neurons are known to lose viability following prolonged $Ca^{+2}$ influx associated with activation of calcium-activated proteases. Minimal signs of cell death were observed in the neuronal cultures monitored for a period of 48 hours following use of the methods and these solutions.

Example 3

Introducing Genetic Material into Living Cells

Ciliary ganglia from chick embryos used in examples herein were dissociated from each other using trituration.

Cells were placed in a small volume (50 μl to 100 μl), and a solution having a high concentration of plasmid cDNA (70 μg/ml) containing a gene that encodes green fluorescent protein (GFP) fusion proteins of interest was added to the cells.

A very fine bore polished glass tube was then used to pass the cells through the tip at high velocity. The fluid was passaged sequentially back and forth through the small bore tip about five to about ten times, into a vessel or receptacle, in this example a 1500 μl Eppendorf microcentrifuge tube. The small volume of cells and plasmid cDNA was almost entirely passaged, which maximized exposing the cells to the DNA during the high velocity transitions. The passaging process was performed while monitoring volumes and minimizing production of bubbles, as extracellular oxygen is toxic to cells. As the cells were passed through the tip of the glass tube, pressure was gradually increased, which prevented bubble formation and improved cell survival among cells in the population treated by the technique. A constant fluid pressure was maintained during fluid passaging, to avoid sudden, instantaneous changes in fluid pressure that damage cells by rupturing the cellular membrane. The methods herein gradually increased or ramped up the fluid flow to avoid damaging the cells. The dampening effect of fluid response to pressure changes also contributed to the ramping of increase in fluid flow. Sudden changes in fluid pressure to initiate or alter fluid flow, were carefully analyzed to determine effect of and thereby reduce damage to the cells for example to avoid rupturing of cell membranes.

The method for initial dissociation and high velocity passaging of the cells was performed in a solution that was substantially free of or had a low concentration of calcium, and that included a high concentration of magnesium (from 1.5 mM to 5.0 mM). This solution was designed to protect the cells, for example neurons, from calcium influx, calcium challenges, and resultant calcium-mediated cell death through activation of calcium-dependent proteases. Such activation of calcium-dependent proteases is specific to the type of cell treated, and therefore higher or lower concentrations of calcium or magnesium were used in Examples herein according to the type of cell.

Figure 3:
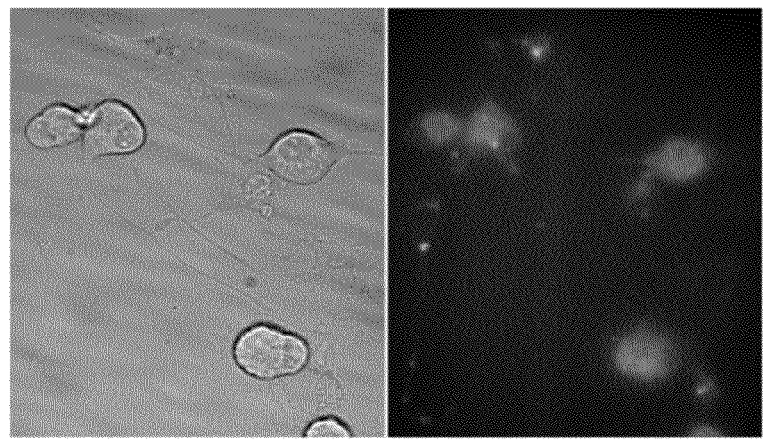
FIG. 3 is a set of photographs showing cells photographed under different detection conditions. The photograph on the left is a photograph of a brightfield microscope field of view showing a collection of ciliary ganglion neurons carrying a gene for green fluorescent protein (GFP) introduced by the methods and devices herein, photographed at seven hours after culturing. The photograph on the right is a photograph of an epifluorescence microscope field of view of the same ciliary ganglion neurons as in FIG. 3 left, photographed at the same time.

Following passaging with nucleic acid, cells were collected by centrifugation in a microcentrifuge at 3000 rpm, or any other rotational rate sufficient to forming a pellet, and the supernatant was removed from the cell pellet, and was replaced with fresh culture medium. The cell pellet was gently re-suspended in medium, and the cell suspension was cultured on plates. Expression of GFP gene and GFP fusion protein was monitored and these proteins were observed to have been expressed as fluorescence was observed within three to six hours in the cell bodies of each of the neuronal and the nonneuronal cells found in the ganglia population. See FIG. 3 and FIG. 4.

A control vector constructed from Sindbis virus was used to tranfect cells, and recipient cells were observed to not express encoded protein until at least about 12 hours after transfection of the cells. The methods and devices herein were thus observed to have achieved visible GFP expression, within a fraction of the lag time of the method using Sindbis virus, and lag in expression time was reduced by about 50% to about 75%.

Example 4

Expression of Myosin Va

A gene encoding a GFP-myosin V fusion protein was introduced into chick ciliary ganglion neurons. Movement of GFP-myosin Va-positive membrane compartments within axons and cell bodies was observed and the localization of GFP-myosin Va was consistent with cellular localization of myosin V in control untreated cells in vivo. See FIG. 6 and Table 1 below.

Myosin Va is a large multi-domain protein (190 kD), therefore observing rapid expression from a relatively long plasmid required of the genes encoding such a large protein, was surprising. Expression of GFP-myosin Va was initially observed using the methods and devices herein within three hours, and by six hours punctate or localized compartments of fluorescence were observed.

These data show that expression of the myosin was associated with directed motion that is typical of membrane compartments, the motion conveyed by the motor activity of myosin Va or associated motor proteins such as kinesin, which bring myosin Va-linked membrane compartments to the periphery along microtubules. Distribution and amount of expression of the GFP-myosin Va construct and the GFP construct each increased in abundance slowly during 24 hours following introduction of the construct.

Example 5

Kinetics and Localization of Expression

Expression of GFP was observed to increase slowly for 24 hours after transfection of the cells with constructs using the methods and devices herein. At 24 hours, GPF protein was observed to have been expressed diffusely throughout the cell, and was also observed in intensely-fluorescent membrane compartments within the cytoplasm of the cell. See FIG. 3.

The frequency (number of cells randomly sampled, and percent) of GFP protein control expression (GFP) or GFP-myosin Va construct (Myosin Va) expression in neuronal and nonneuronal cells, observed as a function of time after transfection using the method herein, including plating the cells in culture, is shown in Table 1. It was observed that nonneuronal cells required a greater time period for appreciable expression, and that neurons show consistently high frequencies of expression in either a diffuse form early after culturing, or in the form of punctate or compartmentalized staining later after culturing. Without being limited by any particular theory or mechanism of action, it is envisioned that the observed staining is related to a relatively high metabolic activity of neurons growing in culture.

TABLE 1

Frequency in cells of gene expression observed as a function of time

| Time (h) after culturing | GFP stain | GFP total | GFP % | Myosin Va stain | Myosin total | Myosin Va % |
|---|---|---|---|---|---|---|
| Neurons | | | | | | |
| 3 | 5 | 5 | 100 | 17 | 17 | 100 |
| 4 | 18 | 18 | 100 | 15 | 15 | 100 |
| 5 | | | | 23 | 26 | 88.5 |
| 7 | 44 | 45 | 97.8 | 30 | 30 | 100 |
| 21 | | | | 22 | 22 | 100 |
| Nonneuronal cells | | | | | | |
| 3 | 0 | 4 | 0 | 5 | 18 | 27.8 |
| 4 | 3 | 6 | 50 | 0 | 2 | 0 |
| 5 | | | | 11 | 20 | 55 |
| 7 | 26 | 32 | 81.2 | 21 | 37 | 56.8 |
| 21 | | | | 33 | 35 | 94.3 |

Figure 4A:
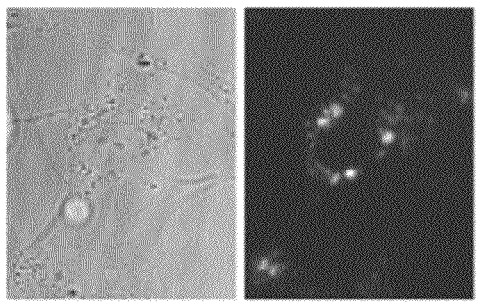
FIG. 4 panel A is a set of photographs each showing a nonneuronal ciliary ganglion cell that is the recipient of a gene encoding green-fluorescent protein (GFP), introduced by the methods and devices herein. The photograph on the left is a brightfield microscope field of view, and the photograph on the right is an epifluorescence microscope field of view showing GFP fluorescence as light areas in the cell.
Figure 4B:
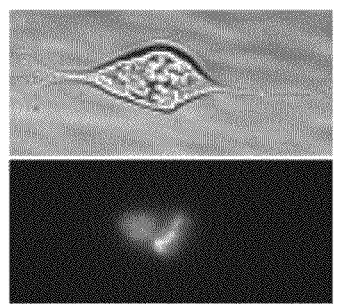

Expression of GFP protein in nonneuronal and neuronal cells was determined to achieve a maximum at 48 hours after the time of loading/introduction (See FIG. 4). GFP protein expression was observed to be abundant in compartments in the cytoplasm, and was mostly absent from the nucleus. FIG. 4.

Figure 5A:
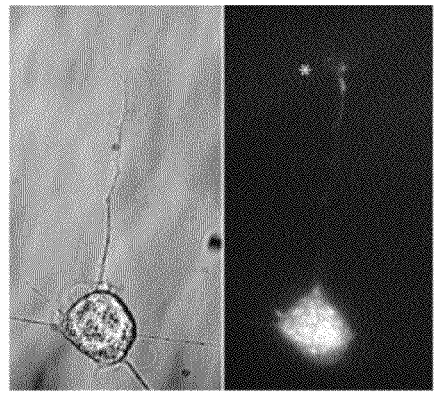
FIG. 5 panel A is a set of photographs each showing a ciliary ganglion neuron that is the recipient of a gene encoding GFP-myosin Va fusion protein, introduced by the methods and devices herein, photographed at time point eight hours after having the genetic material introduced into the cell. The photograph on the left is a brightfield microscope field of view, and the photograph on the right is an epifluorescence microscope field of view, each taken at the same point in time. The photographs of the cells treated with GFP-myosin Va gene by methods described herein show a specific distribution in the neuronal processes typical of native myosin protein.
Figure 5B:
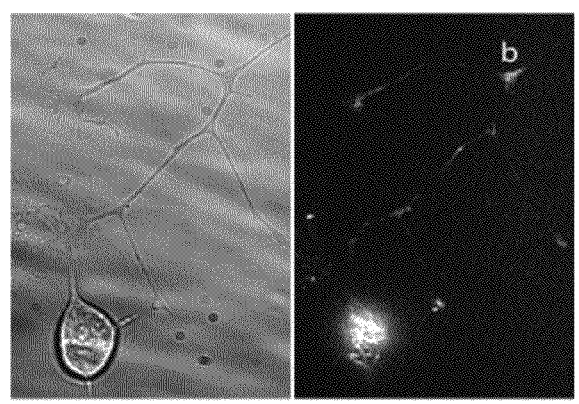

Strong evidence of localization of myosin Va was observed both in the cell body and the neuronal processes. Localization was observed particularly in branch points and tips of growing axonal processes. FIG. 5 Panel A and Panel B. Data in Examples herein demonstrate successful transfection of neuronal cells with genes encoding different myosin Va constructs, with substantial expression observed in the cells.

Figure 6A:
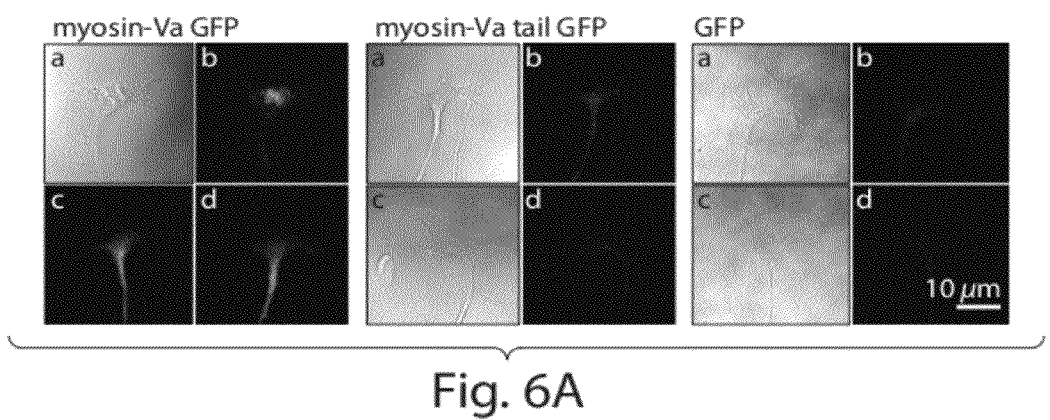
FIG. 6 is a set of photomicrographs and bar graphs showing effects entry of genetic material by methods described herein observed on fluorescence abundance of the tips of neuronal projections (growth cones), and filopodial length, respectively. Cells were transfected with a each of a construct carrying a gene encoding enhanced GFP-myosin Va (myosin-Va GFP), an enhanced GFP-myosin Va that includes only the tail region (myosin-Va tail GFP) and therefore does not bind the actin cytoskeleton, or a control GFP construct (GFP). Cells were transfected and probed for fluorescence after 15 hours in cell culture. Each pair of images of a single cell in FIG. 6 panel A includes a brightfield (Nomarski or differential interference contrast microscopy, DIC) micrograph on the left and a matched fluorescence image of the same cell on the right, apart from images c and d which are additional examples of growth cones with abundant enhanced GFP-myosin Va.
Figure 6B:
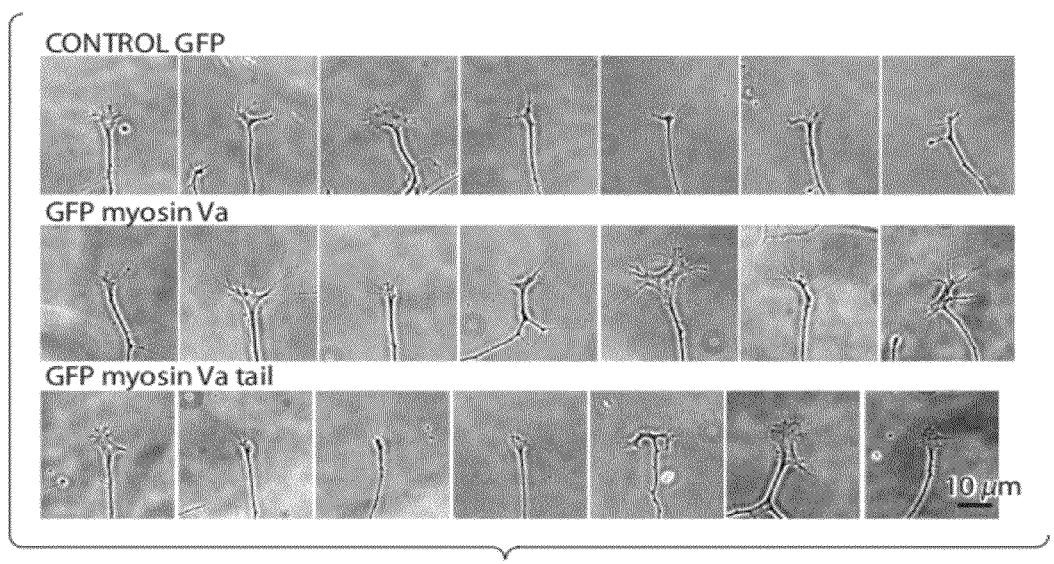
Figure 6C:
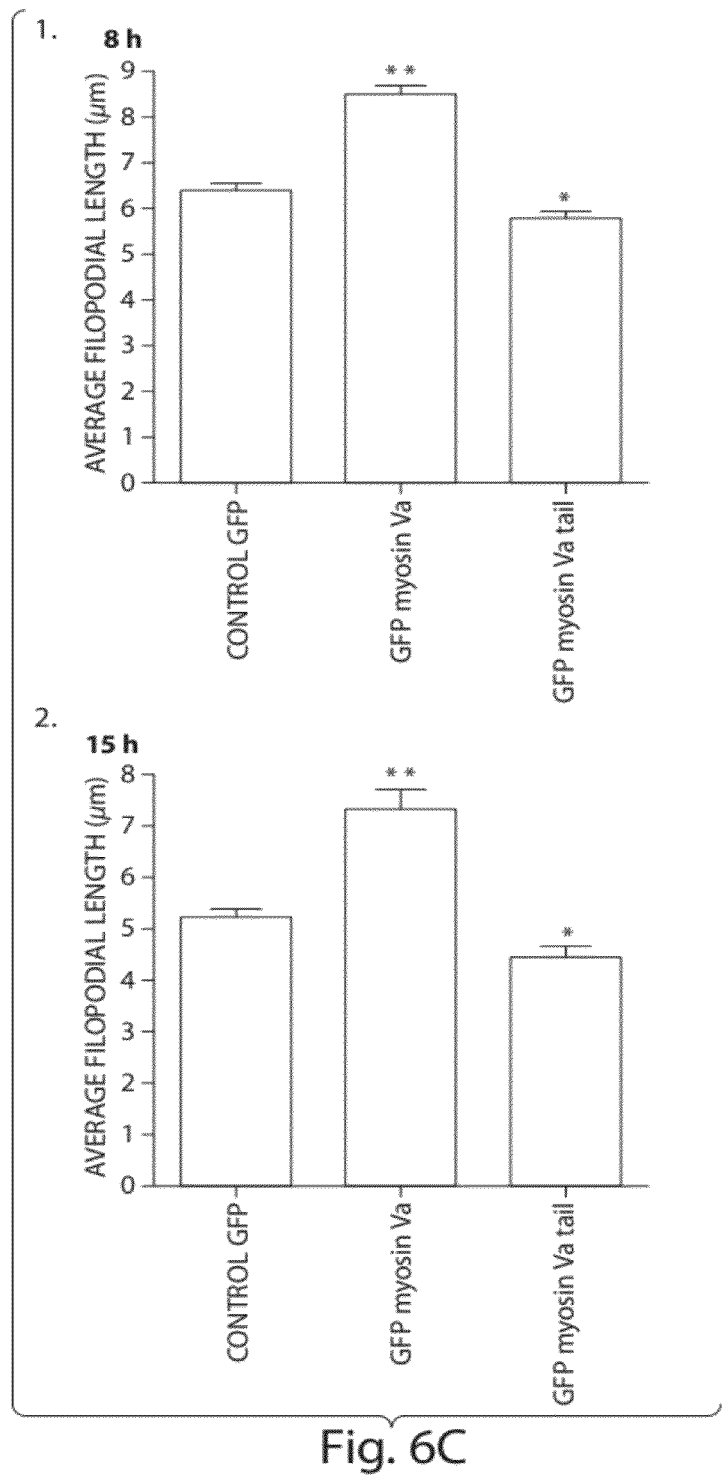

Transfection was observed to result in specific changes in nerve cell projections at the growing tips. Changes were observed in neuronal filopodia, the finger-like projections of growing tips (FIG. 6). Transfection of enhanced GFP-Va tail was observed to result in a slight but significant reduction in filopodial length ($p<0.01$, Student's t-test) at 15 hour compared to eight hours. Number of filopodia/growth cones for each construct group include: control GFP (538/59), enhanced GFP-myosin-Va (630/69), and enhanced GFP-Va tail (653/76). The data show that overexpression of myosin-Va resulted in increased filopodial lengths, and expression of a truncated form of myosin-Va, which does not bind actin filaments, resulted in reduced filopodial lengths. These data show successful transfection and function of transfected myosin-Va constructs in primary neurons using the methods and devices herein, and expression of differential phenotypes related to functions of the encoded genes.

Example 6

Expression of Genetic Material in Mouse Sperm Cells

The methods and devices herein were applied to a cell system, the mature sperm cell, in which introduction and expression of genetic material has not heretofore been observed. Sperm cells are notoriously difficult to permeate, and have been characterized as having no nuclear translation and very little RNA. Protein synthesis in sperm cells is confined to mitochondria within the small amount of mature sperm cytoplasm. Thus, sperm cells have largely been considered inaccessible to methods of recombinant DNA technology.

Figure 7:
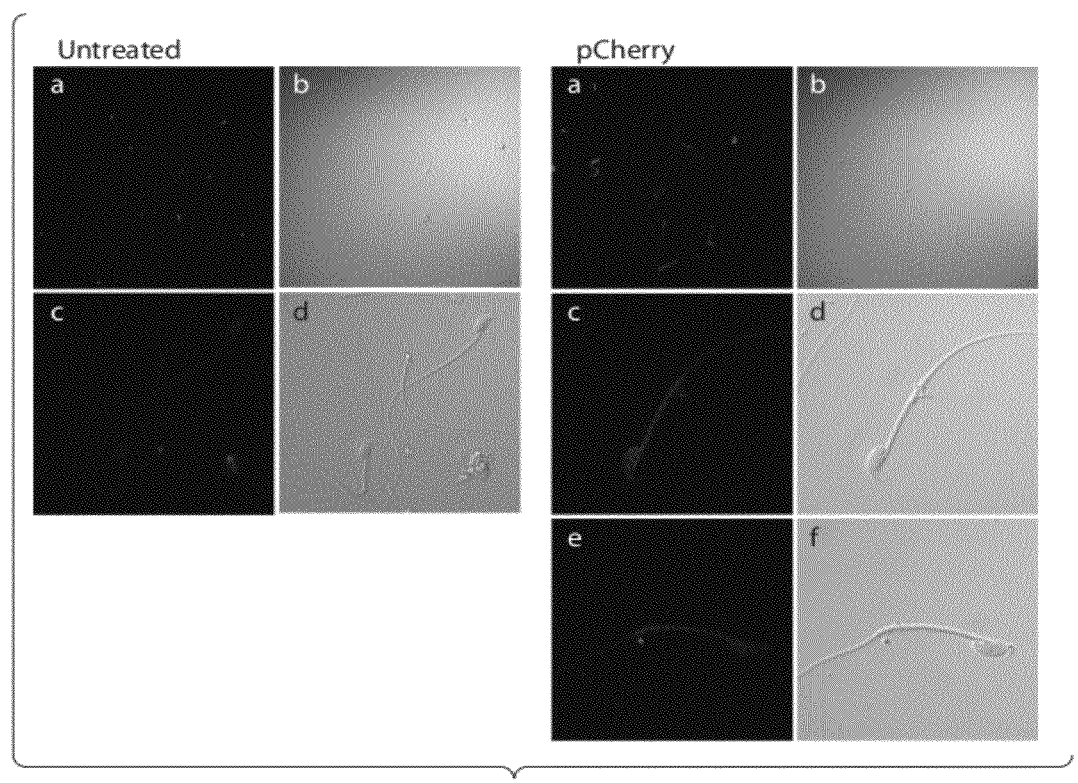
FIG. 7 is a set of pairs of photographs each pair showing untreated sperm cells (Untreated) on the left, and the same sperm cells that were transformed by methods and systems herein with a fluid containing a plasmid encoding a variant of green fluorescent protein, the variant entitled pCherry (Shaner N C et al., 2004, Nat Biotechnol 22(12):1567-1572), on the right (pCherry) and untreated controls on the left. Dark field photographs on the left (panels a, c, and e) are taken with fluorescence microscopy, and on the right (b, d, and f) Nomarski optics (differential interference contrast microscopy). Panels (a) and (b) show a low power field of view of a group of treated (pCherry) sperm cells. Panels (c) to (f) show high power fields of different views of sperm cells with prominent pCherry fluorescence. Fluorescence intensity in untreated control cells was attributed to background autofluorescence (fluorescence native to the cell). Panels (a) and (b) show a low power field of view with many sperm cells. Bright fluorescence points are debris from other cell types. Panels (c) and (d) show a higher power field of view illustrating the background level of nonspecific fluorescence in untreated sperm cells from the same field as in (a) and (b). In the right panel of images (pCherry transfected) sperm cells using methods and devices herein show expression of pCherry protein as demonstrated by significant fluorescence throughout the cells especially in the sperm head and midpiece, with a lesser amount observed in the principle piece, or sperm tail.

The methods and devices in Examples herein were used to introduce a plasmid encoding pCherry, a variant of GFP protein, that fluoresces in the red part of the visible spectrum (Shaner et al., Nat Biotechnol 22(12): 1567-1572, 2004). The pCherry gene is operatively linked to and controlled by a CMV promoter. Following transfection the living mouse sperm cells were incubated overnight at 37° C. pCherry fluorescence was observed within 24 hours in a subset of treated sperm cells (FIG. 7). These data show for the first time successful expression of a recombinant gene, encoding pCherry protein, in the sperm cells transfected by the methods herein.

Localization of fluorescence of GFP-positive sperm cells was compared with that of a set of control sperm cells treated with a membrane permeable fluorescent dye, Lavacell, which permeates cells and stains internal membranes. Fluorescence of Lavacell stained sperm cells was observed throughout the cell including the cell head, midpiece and tail. See FIG. 7.

In contrast, transfected pCherry expressing sperm cells (not treated with Lavacell) showed essentially no fluorescence in the head portion of the cells. These cells were observed to have intense fluorescence in the midpiece where mitochondria are abundant, with minimal fluorescence in the flagellum or tail segment (FIG. 7). pCherry expression was observed in 75% of the sperm cells at sites of localization, consistent with localization of RNA in sperm cells.

Example 7

Introducing Genetic Material into Cells Using Pressurized Solutions

Genetic material is introduced into a cell in a tissue, or in a monolayer in culture, by ejecting a composition including a genetic material onto the cells in the tissue or monolayer. The genetic material is introduced into the cell/monolayer of cells using fluid pulsed at high velocity which creates conditions similar to that of the methods described herein, such that the increase in fluid speed corresponds to a simultaneous decrease in pressure at the cell membrane. The pulsed fluid momentarily stretches the cell membrane (Bernoulli's principle) and a pore or a plurality of pores is formed that acts as a point of entry for the genetic material.

The fluid containing the genetic material is pulsed at a specific pressure, frequency, or force to form a pressure wave. Alternatively, the fluid is pulsed across the surface of, or directly at the face of, the tissue or monolayer.

It is envisioned that genetic engineering in situ of tissues needing a therapeutic gene is achieved by methods herein, for example, a gene encoding a normal allele of a defective inherited gene, for example, into a hematopoietic tissue such as bone marrow or liver, is delivered by this method.

Example 8

Expression of Genetic Material in Human Endothelial Cells

Human umbilical vein endothelial (HUVEC) cells similar to most primary cells, are characterized by poor transfection rates using previously known transfection methods such as nucleofection, electroporation, and using current transfection products such as lipofectamine. The methods and tip assemblies herein were used to transfect HUVEC cells with a plasmid encoding a fusion protein of enhanced green fluorescent protein (EGFP) and human porcine endogeneous retrovirus receptor (HuPAR2), a protein that is specifically localized in perinuclear subcellular membranous compartments.

Examples herein generated an enhanced GFP (EGFP)-tagged C-terminal HuPAR-2 fusion protein (HuPAR-2/EGFP). The HuPAR-2 open reading frame (ORF) was amplified from the Topo-pCRII clone by using the primers 5'-ACGCGGTACCCAGGGGTCTACACAGTCCTTT-3' (SEQ ID NO: 1) and 5'-ACGCAGATCTAGCATCTTTG-GACCTACCTAG-3' (SEQ ID NO: 2), which contain KpnI and BglII restriction sites. The product was cloned into Topo-pCRII (Invitrogen Life Technologies) and excised using KpnI and BglII. This fragment was cloned upstream and in-frame of the EGFP ORF in the KpnI and BglII fragment of the EGFP fusion vector pEGFP-N1 (BD Biosciences CLONTECH; San Jose, Calif.).

HUVEC cells were grown in ATCC endothelial cell media and were contacted with a vector (35 µg/ml; 7005 base pairs) encoding a fusion protein of EGFP and HuPAR2 suspended in Hank's balanced salt solution (HBSS; Sigma-Aldrich, St. Louis, Mo.). The cells were plated on a glass bottom 35 mM petri dish for 15 minutes to settle and to attach to the surface of the dish. Growth medium was added and the cells were incubated for 24 hours at 37° C. and 5% $CO_2$.

The cells were visualized using a laser scanning confocal fluorescence microscope and contrast-enhanced version of brightfield microscopy, namely DIC (differential interference contrast optics), and fluorescence was analyzed in ten randomly chosen microscope fields 24 hours after transfection. Total number of HUVEC cells and number of cells showing GFP-HuPAR2 fluorescence were determined, and the percentage of HUVEC cells with GFP-HuPAR2 fluorescence was calculated and compared (Table 2). Table 3 shows a statistical analysis of the data.

Figure 8A:
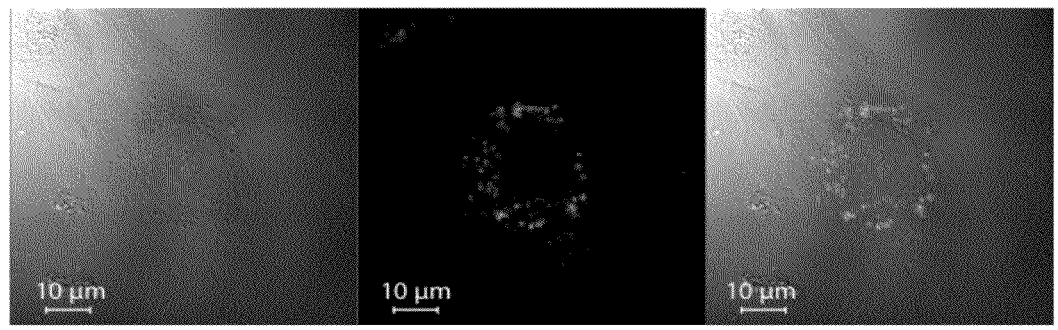
FIG. 8 is a set of photomicrographs showing primary human umbilical vein endothelial cells (HUVEC) 24 hours after a tip assembly was used to transfect cells with a plasmid encoding a fusion protein of enhanced green fluorescent protein (EGFP) and human porcine endogenous retrovirus receptor (HuPAR2). HuPAR2 protein localizes specifically in subcellular membranous compartments surrounding a cell nucleus. The cells were plated on a glass-bottom 35 millimeter Petri dish for 15 minutes for attachment to the dish, and were cultured in growth medium at 37° C.
Figure 8B:
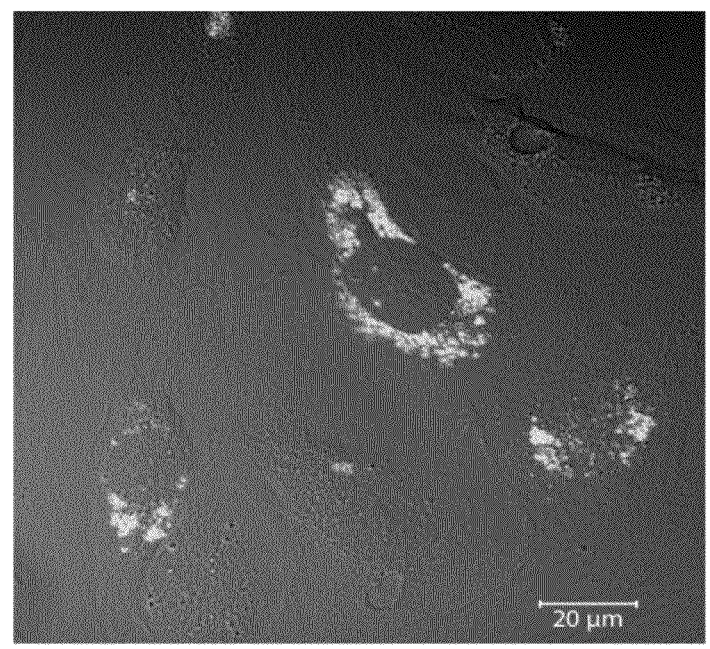

Photomicrographs of the HUVEC cells were analyzed using fluorescence microscopy. It was observed that an average of greater than 70% transfection efficiency was achieved for the cultured HUVEC cells. See Table 2 and Table 3. Representative DIC photomicrograph data and fluorescence photomicrograph data for a single cell and for a plurality of cells are shown in FIG. 8 panels A and B, and these data show that the cells were effectively transfected cells. Dark granules were observed by DIC in the membranous compartments surrounding the nucleus of a single HUVEC cell (FIG. 8 panel A left photomicrograph) and a plurality of HUVEC cells (FIG. 8 panel B). HuPAR2 protein localizes specifically in a perinuclear subcellular membranous compartments, and cells observed herein showed significant GFP fluorescence staining in the perinuclear subcellular compartments of the cells transfected with the GFP-HuPAR2 plasmid using methods and systems herein. FIG. 8 panel A middle photomicrograph. An overlay of the DIC photomicrograph and the fluorescence microscope photomicrograph showed that the GFP-HuPAR2 was localized specifically in the perinuclear membranous compartments. These data show HUVEC cells were successfully transfected using the EGFP-HuPAR2 construct and the methods and the tip assembly herein.

TABLE 2

HUVEC cells show GFP-HuPAR2 fluorescence in 10 randomly chosen microscope fields 24 hours after transfection

| HUVEC cell number per field | GFP-HuPAR2 fluorescent cell number | percent HUVEC cells with fluorescence |
| --- | --- | --- |
| 10 | 7 | 70 |
| 16 | 12 | 75 |
| 10 | 8 | 80 |
| 18 | 17 | 94.4 |
| 16 | 8 | 50 |
| 13 | 7 | 53.8 |
| 20 | 17 | 85 |
| 16 | 12 | 75 |
| 9 | 4 | 44.4 |
| 15 | 12 | 80 |

TABLE 3

Statistical analysis of data shown in Table 2

| | average (x) | standard deviation (sd) | standard error (se) |
| --- | --- | --- | --- |
| total number of HUVEC cells | 14.3 | 3.68 | 1.16 |
| HUVEC cells showing GFP-HuPAR2 fluorescence | 10.4 | 4.35 | 1.37 |
| percentage of total number of HUVEC cells that are Hu-PAR2 fluorescent cells | 70.8 | 16.26 | 5.14 |

As the cells in this Example were transfected with a previously frozen vector, which was a large plasmid (7005 base pairs), the methods and tip assemblies herein were surprisingly more effective in transfecting and transducing cells with a genetic material and under circumstances that by other methods would have proven to be much less efficient.

Example 9

Construction and Adaptations of Tip Assemblies

Tip assemblies suitable for use in methods herein include those constructed of a variety of different types of materials, and in different sizes and shapes. Fluids having cells and materials are introduced into the tip assemblies, and the effectiveness of the tip assemblies to introduce material into cells is determined by one skill in the art of cell transfection.

Adaptation of design of the tip assemblies includes producing structures with varying fluid path shapes, number of constriction portions, and by varying concentration of materials in the composition including the presence of organic and inorganic agents.

Tip assemblies can be used with various known types of reservoirs and flow devices. For example the reservoir is a centrifuge tube, a bin, a bag, or a bottle, and the flow device is a hand-held 200 µL pipette or hand pump. Each of the tip assemblies is adapted by obtaining data (e.g., pressure differentials, cell membrane porosity and cell viability) for each of the multiple tip assemblies and each of the varying concentrations of substances in the tip assemblies.

Figure 9:
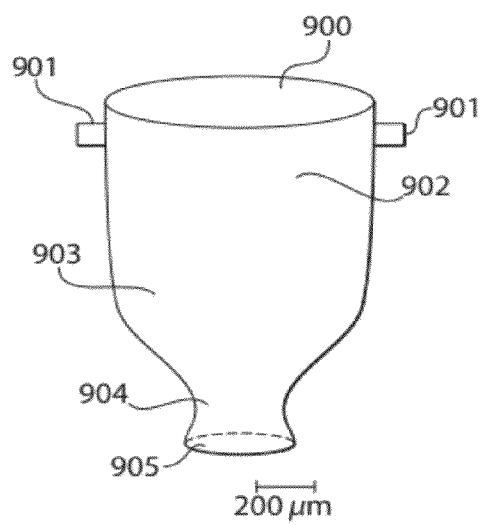
FIG. 9 is a drawing of a three-dimensional representation showing an exemplary shape of a tip assembly having a body including a proximal opening 900, attachment shoulders 901, an attachment portion 902, a channel portion 903, a constriction portion 904, and a distal opening 905. The fluid path direction is from the proximal opening 900 to the distal opening 905 or alternatively from the distal opening 905 to the proximal opening 900. The channel portion 903 was designed to have a greater inner diameter and cross-section area than the constriction portion 904. The scale bar is 200 µm.

FIG. 9 is a drawing of a three-dimensional representation of an exemplary tip assembly having a body including an opening shown at the top which is proximal, proximal opening 900, to the reservoir and the fluid flow device, an attachment portion 902, a tip assembly shoulder 901 for ejecting the tip assembly when attached to a flow device, a channel portion 903, a constriction portion 904, and a distal opening 905 shown at the bottom. The fluid path direction proceeds from the proximal opening 900 to the distal opening 905. The channel portion 903 has a greater inner diameter and cross-section area than the constriction portion 904. The tip assembly shoulder 901 extends laterally from an outward surface of the attachment portion 902. A lower ejector section of an embodiment of the flow device removes the tip assembly from the flow device.

To operate, a flow device or fluid handling device in certain embodiments is attached to the tip assembly at the attachment portion. The fluid containing cells and material is drawn into the tip assembly from the distal opening through the constriction portion to the channel portion of the tip assembly. The top meniscus of the fluid surface and the end of the flow device are separated by a distance sufficient to avoid contact between the fluid with the flow device, so that different materials can be used in each tip. The fluid device is used to impel the fluid through the channel portion to the constriction and the distal opening, and a reduced pressure in the constriction portion compared to the channel portion is achieved, forming pores in cells containing within the fluid, and a material included in the fluid is introduced into the cells. In certain embodiments, a fluid containing the cells is drawn into a longer fluid path such that sufficient fluid velocities are attained when passing through the constriction portion of the tip assembly.

The tip assemblies are evaluated under conditions and by the methods used in Examples above. The data obtained are used to determine cell viability and presence of material in the cell. Data show that the tip assemblies introduced material into cells by reducing the fluid pressure of the fluid and by increasing the membrane porosity of cells, in living cells and non-dividing cells. These tip assemblies were shown by Examples herein to be more effective, more efficient and convenient for introducing material into cells than previous methods and devices.

Example 10

Design of an Embodiment of the Transfection System

An embodiment of the transfection system described herein is shown in FIG. 10 panels A-D. The main components of the device are a tip assembly, a computer programmable syringe pump 101, 102 connected to the tip assembly by means of a USB converter 103 and an RS232 interface 104, and a power supply 110. As shown in FIG. 10 panel A the syringe pump 101,102 is attached to the inner side of the metal lid 105 of a jump box 106. The USB converter 103 and the RS232 interface 104 that connects the syringe pump to an external computer are also attached to the inner side of the metal lid 105 of the jump box 106. The hardware is not visible during use of the device in laboratory. An external computer communicating through the RS232 interface 104 and the USB converter 103 is used for controlling the syringe pump 101,102 using the data analysis software MATLAB (Mathworks, Natick, Mass.). Alternatively the transfection device uses a simple graphical user interface software, LabWindows/CVI Run-Time Engine 8.5.1 (National Instruments, Austin, Tex.).

Figure 10A:
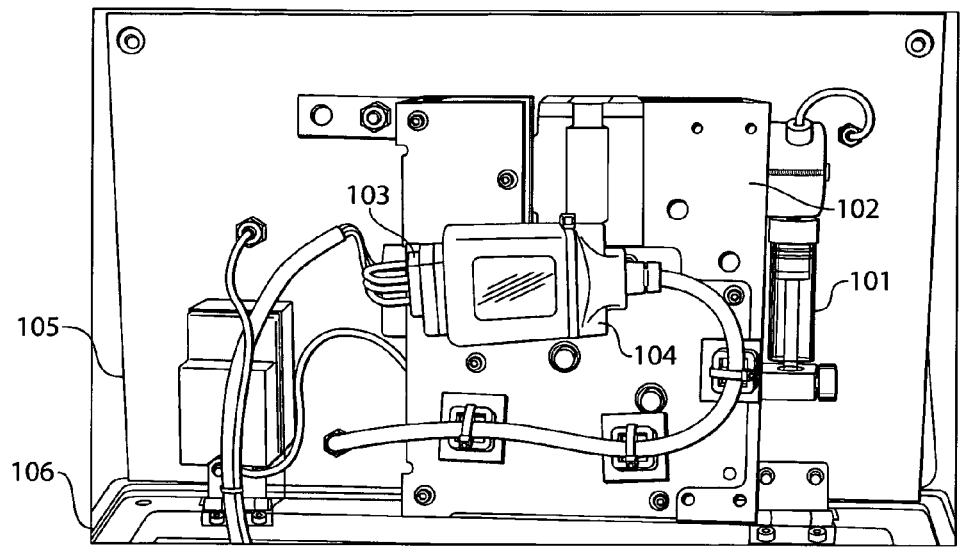
FIG. 10 is a set of photographs of an exemplary transfection system.
Figure 10B:
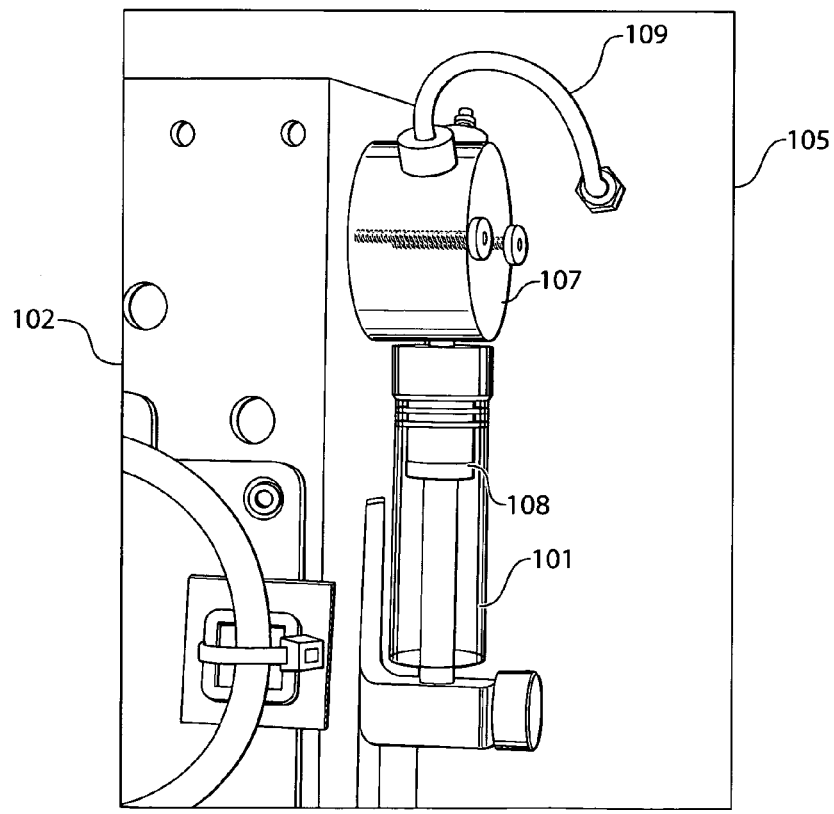
Figure 10C:
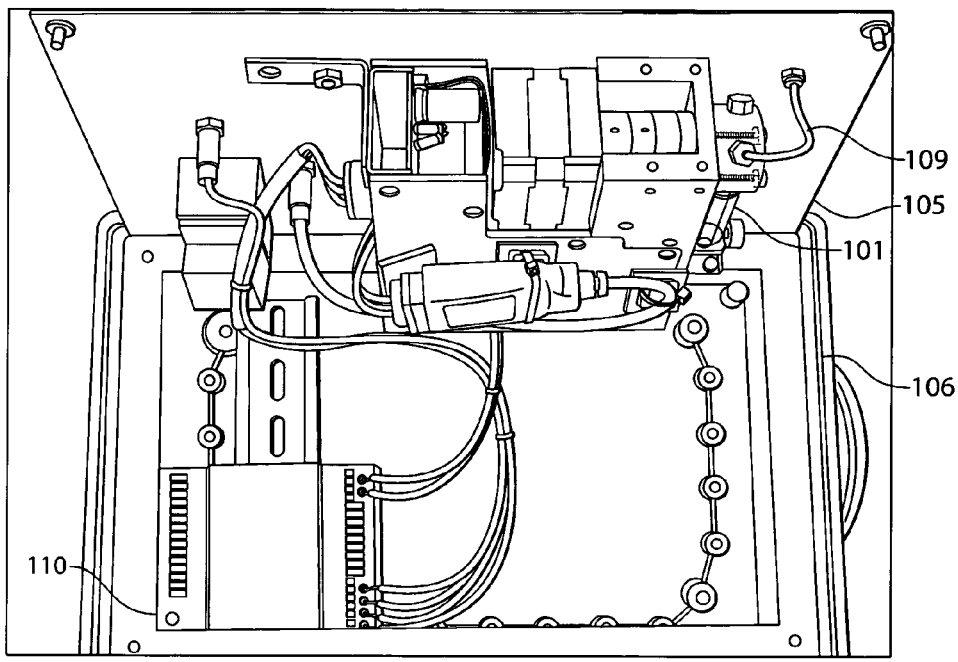
Figure 10D:
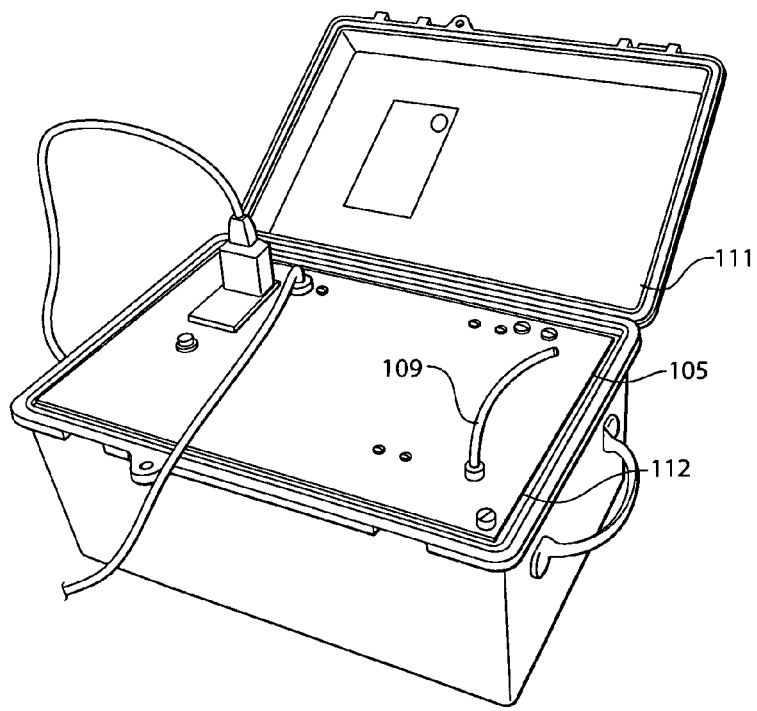

The position of the programmable syringe and the pump mechanism 101,102 on the jump box 106 right is shown in FIG. 10B. The borosilicate glass syringe 101 has a UHMWPE (ultra-high molecular weight polyethylene) seal 107 for lubrication and solvent resistance. A TYGON® tube 109 extends through the metal lid 105 of the jump box 106 and connects to the proximal end of a soda lime glass capillary tube (the tip) through additional tubing. The capillary tube is an exemplary tip (FIG. 1 panel A) having the dimensions: inner diameter 1.1-1.2 mm, wall thickness 0.2 mm, length 75 mm.

The power supply 110 is located inside the jump box 106 to the lower left (FIG. 10 panel C). The power supply 110 is a single phase 24V, 2.5A power supply (PHOENIX CONTACT GmbH & Co. KG, Step Power, Blomberg, Germany), standard for distributor boards and flat control panels. The power supply (110) has low standby losses and high efficiency. Alternatively, a power adaptor is FSP60-11 (FSP North America), having 24V, 2.5A output. The power sources take 100-240V, 2.0A, 50-60 Hz input.

As shown in FIG. 10 panel D, the jump box 106 is located in a tissue culture flow hood for sterile conditions. During use the metal lid 105 remains in the closed position and the outer lid in an open position 111.

Example 11

Fluid Cycling Parameters During Transfection

This example illustrates the general flow parameters during fluid cycling through the tip of the tip assembly used in the methods and system or devices described herein.

Figure 11:
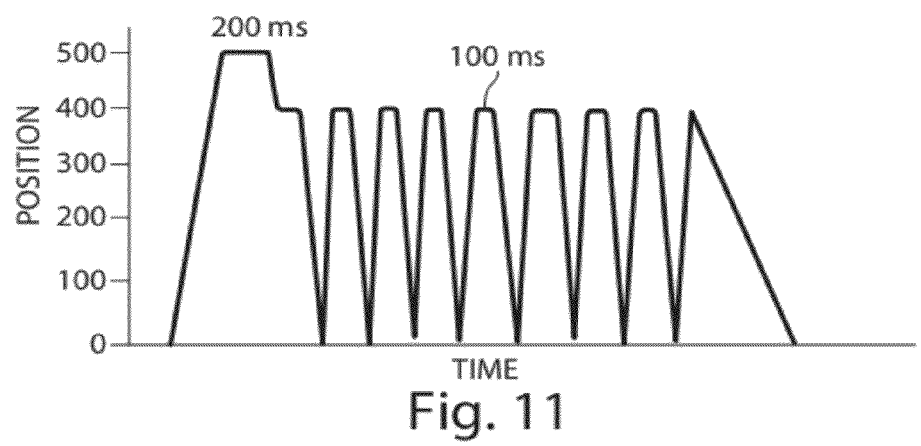
FIG. 11 is a schematic drawing illustrating exemplary movement of the syringe plunger 108 in fluid cycling with eight cycles. The return stroke operates according to the same parameters as the execution stroke, i.e. outflow motion has the same characteristics as inflow motion. A cycle consists of an execution stroke followed by a return stroke. The position of the plunger location along the length of syringe at a time point during a cycle is represented on the ordinate, and time is represented on the abscissa. The plunger initially moves from position 0 to position 500, the load position, pauses for 200 milliseconds (ms), and moves downward to position 400, which reduces the fluid volume to less than an initial fill volume, leaving a cycling volume in the tip. After a 100 ms pause the plunger ramps from position 400 to 0. Each ramp is shown have a starting velocity, a final velocity and an acceleration from the starting to the final velocity.
Figure 12A:
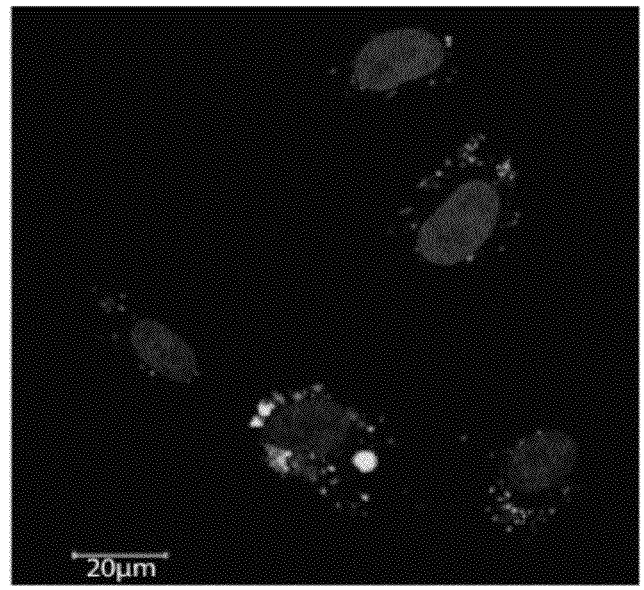
FIG. 12 is a set of confocal fluorescence microscope images of primary HUVECs (human umbilical vein endothelial cells) transfected with a plasmid using the methods and apparatus herein, encoding a fusion protein EGFP-CDC42 (enhanced green fluorescent protein-cell division control protein 42). Scale bars are 20 µm.
Figure 12B:
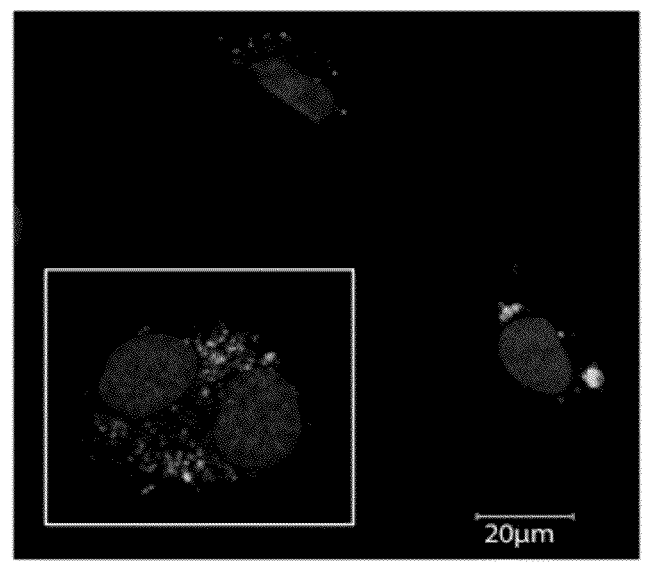
Figure 12C:
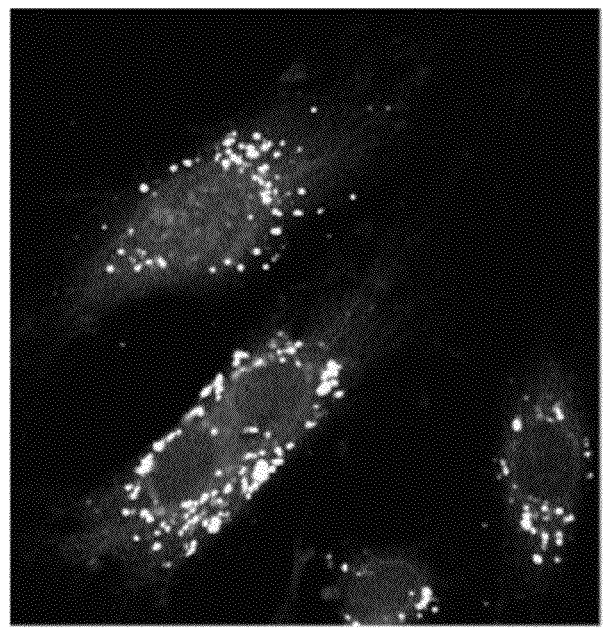
Figure 12D:
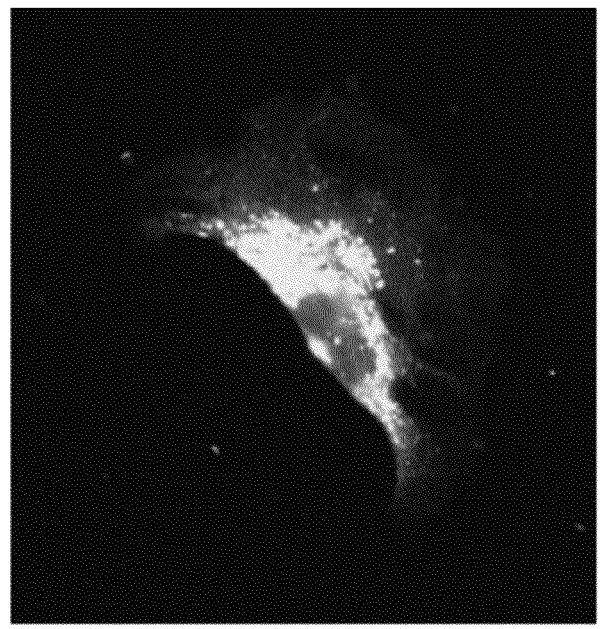

A mixture containing cells and a composition to be introduced into the cells in a fluid is drawn into and forced out of the tip of the transfection device herein iteratively, resulting in cycles of inflows and outflows. An execution stroke followed by a return stroke constitutes a cycle. The return stroke and the execution stroke operate according to the same parameters. The programmable syringe 101,102 described in Example 10 produces the flow cycles. A schematic drawing illustrating movement of the syringe plunger 108 in an embodiment of fluid cycling is shown in FIG. 11, with time represented on the abscissa and the position along the length of syringe at which the plunger is located at that time during a cycle represented on the ordinate.

The following command sequence was used in this embodiment:
/1L14v400V900c200A500M200gL20v100v1000c1000A 400M100A0G8L14v400V900c200A0R The plunger motions and associated parameters in this command sequence proceeding from left to right are described herein. The plunger positions in the command sequence correspond to plunger positions indicated on the ordinate in FIG. 11 with the letter A added as a prefix. For example, plunger position 500 in FIG. 11 is position A500 in the command sequence. FIG. 11 illustrates eight cycles which were performed as follows:

L14 is the initial velocity ramp (acceleration), v400 is the starting velocity and V900 is the maximum velocity during this ramp. A500 is the position the syringe plunger (108) moves to initially, loading the tip. A500 is called the load position. c200 is the cutoff velocity when the plunger reaches A500. M200 is a 200 milliseconds (ms) pause at the load position. The cycling begins after a 200 ms pause, indicated by g in the command sequence. Ramps of a cycle, excluding the initial velocity ramp which has an acceleration L14, have a maximum acceleration L20, a starting velocity 100 (v100), a maximum velocity 1000 (v1000) and a final or ending velocity 1000 (c1000). A downward movement to position A400 reduces the fluid volume to a less than an initial fill volume, leaving a cycling volume in the tip. M100 indicates a 100 ms pause after which there is a ramp from position A400 to A0. This represents the end of the first cycle and is indicated by G in the command sequence. The number 8 indicates that this command sequence has 8 cycles. The first cycle differs from subsequent cycles as it includes the loading step. At the end of the command sequence is a cycle with velocity ramp L14, starting velocity v400, maximum velocity V900, end position A0, and final velocity c200. The letter "R" at the end represents an execute code.

In the examples described herein similar cycles were used with cells and plasmid DNA or siRNA or miRNA.

Example 12

Introduction of EGFP-CDC42 Plasmid into HUVEC Cells

The methods and system or device herein were tested to transfect a primary cell which are more delicate and usually more vulnerable to transfection than transformed cells that have been propagated in the laboratory for many years. Primary HUVECs (human umbilical vein endothelial cells) were chosen for this purpose.

HUVECs were transfected with a plasmid encoding an EGFP-CDC42 (enhanced green fluorescent protein-cell division control protein 42) fusion protein. The plasmid concentration mixed with cells was 70 μg/ml. Cells were allowed to become confluent by culturing them for two days prior to transfection, trypsinized to detach the cells from the cell culture substrate and suspended in fluid for transfection.

Transfection was performed using the parameters: fluid acceleration 6 μl/s/s, flow rate 160 μl/s, cycling volume 50 μl, and two continuous sets of cycles each set having 25 inflows and outflows of fluid through the tip impelled by a 2.5 ml syringe. A volume of 63 μl contained 500,000 cells and the plasmid.

Images of cells taken with a laser scanning fluorescence microscope 24 hours after transfection showed punctate (or spotted) subcellular EGFP-CDC42 fluorescence. The fluorescence was cytoplasmic and in the periphery of the cell, consistent with CDC42 localization, and was excluded from the nucleus (FIG. 12 panel A). Fluorescent cells in twenty randomly selected 20× magnification microscope fields were sampled. Results showed that a pooled average of 88.2% (135/153) of the cells displayed a CDC42 like EGFP fluorescence. Transfection using AMAXA Nucleofactor™ (Lonza Cologne GmbH, Cologne, Germany) electroporation unit was tested for comparison and either no transfection or lower transfection efficiency (less than 30%) was observed.

Images of transfected HUVEC cells with EGFP-CDC42 plasmid using the methods and the transfection device herein include one of EGFP expression in cells that had divided before imaging (FIG. 12 panel B). Consistent with the expression pattern of a protein with a role in cell division EGFP fluorescence was localized to a region between the daughter cells.

EGFP fluorescence of HUVEC cells transfected with EGFP-CDC42 using methods and the transfection device described herein was observed at normal PMT sensitivity and compared with that observed at higher PMT sensitivity (FIG. 12 panel C and D). At normal PMT sensitivity most of the fluorescence was observed to be localized to large granules (FIG. 12 panel C). At higher PMT sensitivity EGFP-CDC42 expression was detected in a subset of cells within numerous subcellular granules which were smaller in size (FIG. 12 panel D). Scanning at a higher PMT sensitivity was observed to offset potential autofluorescence observed in the large granules at normal PMT sensitivity. The fluorescence in the smaller granules was tested by photobleaching using high-sensitivity laser light in scanning mode and was observed to be specific to the expression of EGFP-CDC42 fusion protein.

The example above demonstrates that the methods and devices described herein not only led to efficient transfer of the plasmid into a primary cell, the plasmid was transcribed into mRNA, the mRNA translated into protein and the protein was expressed with correct localization, thereby leading to a successful transfection.

Example 13

Introduction of 7 Kb EGFP-Actin Plasmid into HUVEC Cells

Success in transfection can also be tested using measurement of mRNA copy number following transfection. Measurement of mRNA copy number is useful in situations such as when the fluorescence signal is faint either due to the peculiar nature of the fluorescent protein being expressed or when there is a high autofluorescence background.

Primary HUVEC cells from P5 mouse were transfected with a 7 kb plasmid encoding EGFP-actin fusion protein using methods and device described herein to observe expression of EGFP-actin in actin filament component of the cell cytoskeleton. 500,000 cells were suspended in 100 μl of phosphate buffered saline in a 1500 μl centrifuge tube to which the EGFP-actin expression plasmid at a final concentration 70 μg/ml was added and mixed with the cells.

Parameters used for transfection were: fluid acceleration, 6 μl/s/s, flow rate, 160 μl/s, cycling volume 60 μl, volume of syringe used, 2.5 ml, and sequential passage cycles consisting of three consecutive sets of 25 cycles of fluid motion through the tip. Cells were grown in culture for 48 hours and mRNA production resulting from the transfection was assessed using a method that determines the exact copy number of mRNA per cell. Shih et al. 2005, Exp Mol Pathol 79:14.

Figure 13A:
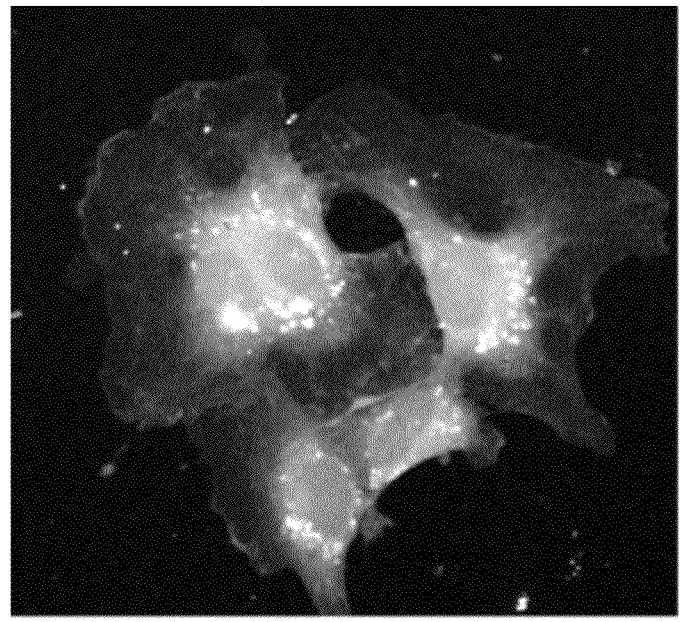
FIG. 13 is a set of confocal fluorescence microscope images and a bar graph showing data obtained from primary HUVEC cells transfected using the methods and the devices herein with a 7 kb plasmid encoding an EGFP-actin fusion protein.
Figure 13B:
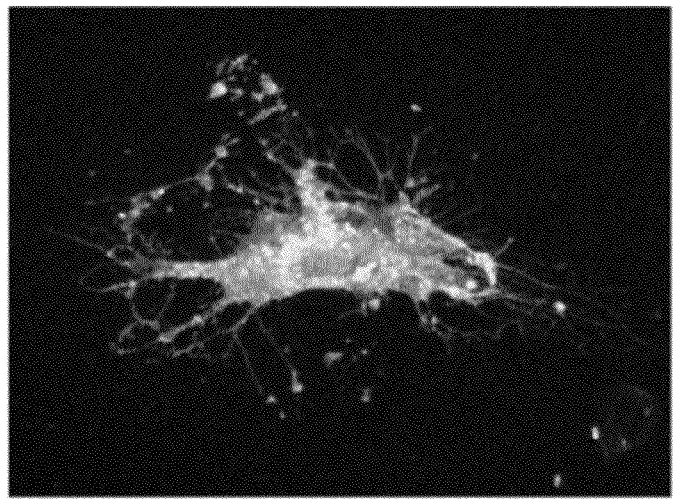
Figure 13C:
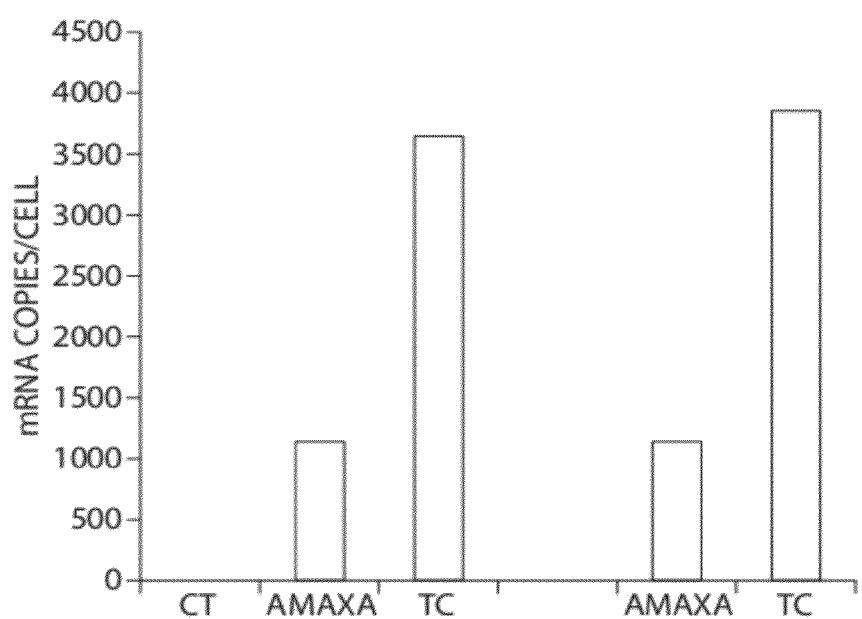

The results are shown in FIG. 13 panels A, B and C. Cells transfected with the transfected device herein are labeled as TC in FIG. 13C. As a control cells were also subjected to the transfection protocol in the absence of the plasmid. These cells were also examined for EGFP-actin mRNA copy number (labeled CT in FIG. 13 panel C). Cells were also transfected using the AMAXA Nucleofector™ electroporation unit and are labeled as AMAXA in FIG. 13 panel C. Cells transfected using the AMAXA Nucleofector™ electroporator resulted in the generation of an average of 1152.75 copies of mRNA per cell against a background of only 0.08 average copies of mRNA per cells for the control cells. In contrast, cells transfected with the transfection device resulted in an average of 3652.66 copies of EGFP-actin mRNA per cell (FIG. 13 panel C). In another experiment performed under similar conditions, comparable average mRNA copy numbers were observed (1152.75 copies of mRNA per cell for transfection with AMAXA Nucleofector™ electroporator versus 3853.95 copies of mRNA per cell for transfection with the transfection device described herein). These results show that transfection using the transfection device described herein resulted in dramatically increased copy numbers of EGFP-actin mRNA per cell and the increase was reproducible.

Thus mRNA copy number measurements also confirmed that methods and devices described herein are useful to achieve efficient transfection even in a primary cell.

Example 14

Introduction of Genetic Material into Jurkat Cells

Figure 14:
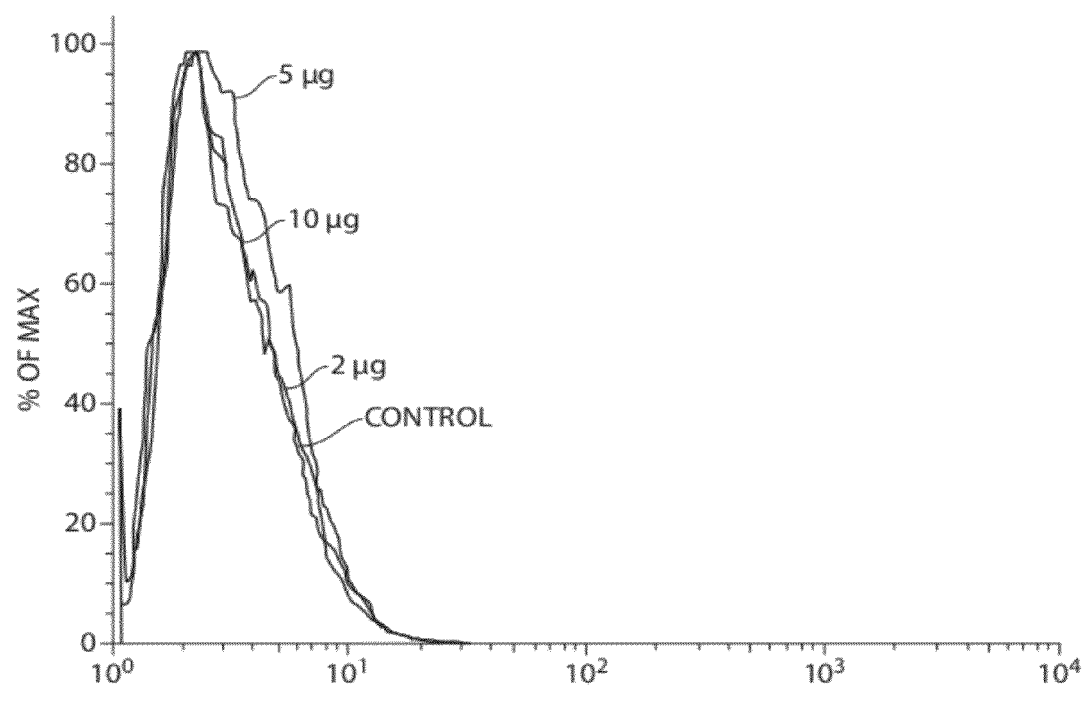
FIG. 14 is a line graph showing quantification of EGFP fluorescence of Jurkat cells transfected with different amounts (2 µg, 5 µg or 10 µg per 50 µl fluid volume) of a plasmid encoding EGFP. Cells treated with 5.0 µg of plasmid showed greater EGFP fluorescence than the background fluorescence observed in control cells.
Figure 15A:
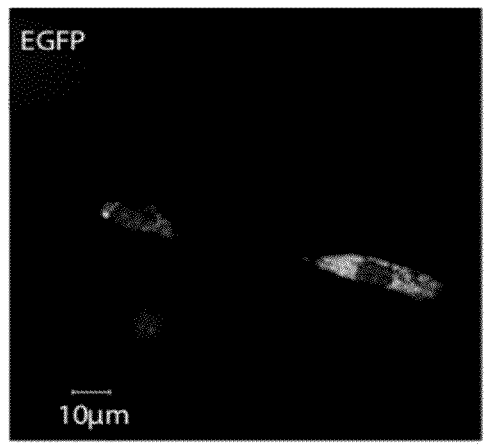
FIG. 15 is a set of confocal microscope fluorescence images of primary mouse brain astrocytes transfected using methods and device herein with EGFP plasmid or Cy3-labeled miRNA. Scale bar is 10 µm.
Figure 15B:
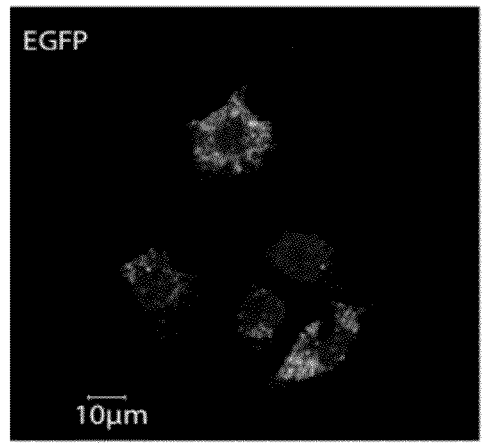
Figure 15C:
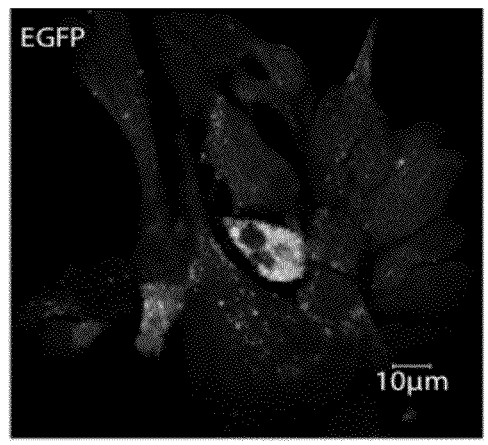
Figure 15D:
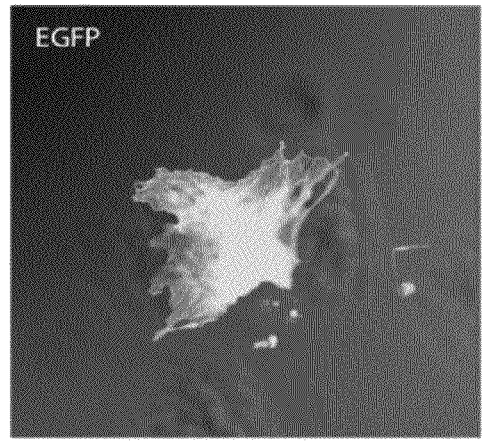
Figure 15E:
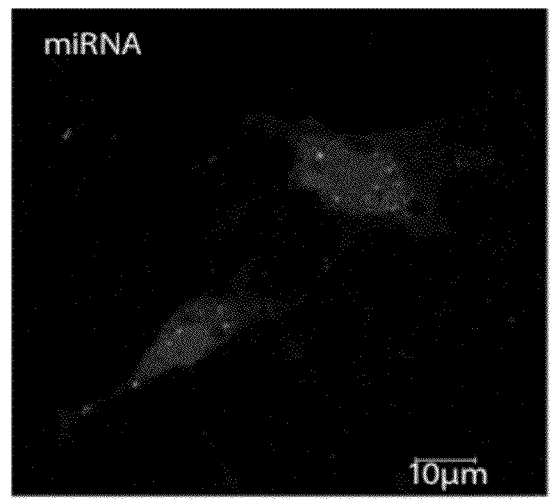
Figure 15F:
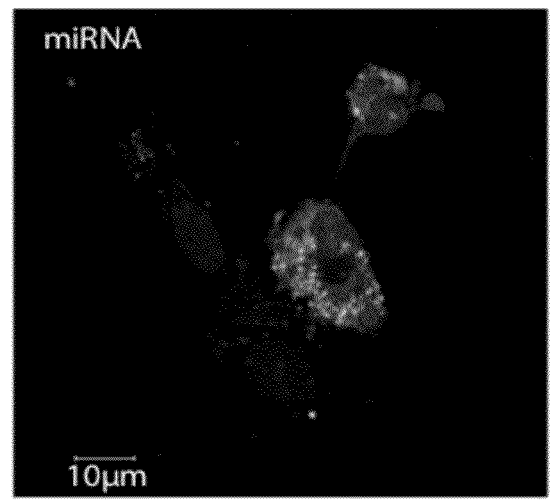

Jurkat cells, a cell type known to be refractory as transfection recipients were tested for transfection efficiency with EGFP (Addgene, Cambridge, Mass.) using the methods and the apparatus herein. Approximately 250,000 cells were suspended in 50 µl of transfection medium, HBSS (Hanks Balanced Salt Solution, Invitrogen Carlsbad, Calif.) absent calcium or magnesium and contained 0.2% w/v EDTA (ethylenediamine tetraacetic acid). As control a mock transfected sample was transfected absent plasmid. Other transfections contained 2.0 µg (55 µl total volume with cells, 36 µg/ml), 5.0 µg (62.5 µl total volume with cells, 80 µg/ml) or 10.0 µg (75 µl total volume of cells, 130 µg/ml) of plasmid. Transfection parameters were: fluid acceleration 6 µl/s/s, flow rate 160 µl/s, cycling volume 60 µl using the 2.5 ml syringe and continuous cycling consisting of 25 inflows and outflows through the tip. Cells were grown in culture for 48 hours and EGFP fluorescence (in FL1-H channel) was quantified using flow cytometry (FIG. 14).

It was observed that 10% of the cells showed 50 to 90% of maximum intensity of EGFP fluorescence. Data obtained from cells treated with 5.0 µg of plasmid showed EGFP fluorescence higher than the background level observed in the control transfection absent plasmid. Fluorescence intensities observed using either 2.0 or 10.0 µg of plasmid were at the background level.

Example 15

Transfection of Primary Mouse Brain Astrocytes Using the Transfection System Herein The methods and transfection system or device described herein, with some modifications were used to test transfection of another type of primary cells.

Primary astrocytes (1 to 2 million cells) were isolated from mouse brain and suspended in DMEM culture media (Dulbecco's modified Eagle medium, Invitrogen, Carlsbad, Calif.) and kept in a cell culture incubator (humidified, 37° C. and 5% $CO_2$) until transfection. For transfection cells were centrifuged and resuspended in 100 µl of HBSS ($Ca^{2+}$/$Mg^{2+}$ free) containing 20 µg/ml of EGFP control plasmid (Invitrogen, Carlsbad, Calif.) or 20 µg/ml of Cy3-labeled miRNA (AM17011, 25 base pair designed RNA oligonucleotide, Arabian, Austin, Tex.)).

The cells were transfected using a tip prepared as follows. A custom fabricated flint glass tube having an ID of 0.88 mm, an OD of 1.23 mm and with wall thickness of 0.14 mm was heated to obtain the curvature as described herein. A further additional microchannel, 250 µm long with a narrowing almost cylindrical portion nearest to the opening of the tip was added to the configuration of the tip. The tip culminated in a small tip opening, diameter 175-200 µM. (FIG. 1 panels C and D).

Transfection with EGFP plasmid was performed using a tip, 200 µm diameter, and transfection with Cy3-labeled miRNA was performed using a tip, 175 µm diameter.

The mixture of cells and the EGFP plasmid or the miRNA were passaged through the tip iteratively for 60-100 times using the methods and transfection device described herein. The mixture was drawn into the tip in a cycling volume of 60-80 µl. In view of the smaller diameter of the tip opening used in this transfection, cycling parameters were modified from those used in Examples 12-14, described generally in Example 11. Only the inflow parameters were changed. Inflow velocity was reduced to 50-80 µl/s and acceleration was reduced to 1-4 µl/s in order to permit unimpeded entry of cell suspension into tip without clogging. Thus assymetric cycles of slower inflow and maximum outflow velocity (240 µl/s) were utilized. After transfection cells were cultured and incubated in a cell culture incubator for three days, then fixed and mounted on glass slides for imaging using a confocal microscope.

Transfection of the primary astrocytes using a tip assembly with narrower tip opening and containing an additional microchannel at the proximal end (FIGS. 1C and D) led to successful transfer of EGFP plasmid or the Cy3-labeled miRNA into the cells. Representative images observed 3 days after transfection are shown in FIG. 15 panels A-F. Panels A and B show cells with varying levels of EGFP fluorescence intensities. Panel C shows a single bright fluorescent cell among a cluster of cells with fluorescence intensities equal to or only slightly higher than background fluorescence. FIG. D is an image showing an overlay of a fluorescence image of a transfected primary astrocyte over a brightfield image of the same cell. The image shows a highly fluorescent transfected cell spread out on a culture substrate having a morphology characteristic of primary mouse brain astrocytes.

Transfection efficiency measured one day after transfection by observing cells having fluorescence above background was determined to be 13.8% (237 cells from 5 different microscope fields). The efficiency was observed to increase to 29.8% three days after transfection (188 cells from 13 different microscope fields).

Panels E and F show transfected primary mouse brain astrocytes that have either a moderate level (panel E) or a high or background level (panel F) of internalized Cy3-labeled miRNA in the cytoplasm of the cells. The miRNA is excluded from the nucleus. The labeled miRNA appear as tiny round fluorescent spots. Transfection efficiency measured 3 days after transfection by observing cells that had fluorescence above background was determined to be 40.9% (41 cells from three microscope fields).

This example further demonstrates the applicability of the methods and transfection device described herein for successful transfection of primary cells, thereby extending the utility of the methods and devices herein.

What is claimed is:

1. A tip assembly for introducing a composition in a fluid into cells comprising:
   an attachment portion open to the atmosphere and proximally fitting a flow device that generates at least one of a positive pressure and a negative pressure for directing the fluid to flow through the tip assembly;
   a channel portion contiguous to and distal to the attachment portion and the flow device;
   a constriction portion contiguous with the channel portion, wherein a constriction portion inner diameter and a constriction portion cross sectional area are smaller than a channel portion inner diameter and a channel portion cross sectional area, wherein a distal end of the constriction portion comprises an opening for ejecting or drawing the fluid, wherein increased fluid velocity and a decreased pressure in the fluid in the constriction portion compared to velocity and pressure in the channel portion enhances formation of membrane pores in the cells, whereby the tip assembly introduces the composition into the cells through the membrane pores, wherein the channel portion curvature and constriction inner curvature characterize a fluid path for the fluid flowing through the tip assembly, wherein the channel portion curvature and constriction inner curvature necessary for introducing the composition into the cells comprises a formula represented in two dimensions is $$f(x) = p1x^7 + p2x^6 + p3x^5 + p4x^4 + p5x^3 + p6x^2 + p7x + p8$$

wherein x is a radial distance from a center axis on the fluid path to an inner surface of the tip and coefficients with 95% confidence bounds in parentheses comprise: p1 is $-2.611e^{-16}$ ($-6.043e^{-16}$, $8.206e^{-17}$), p2 is $3.954^{e-13}$($-3.195^{e-13}$, $1.11^{e-12}$), p3 is $-1.845^{e-10}$($-7.821^{e-10}$, $4.131^{e-10}$), p4 is $1.662^{e-08}$($-2.394^{e-07}$, $2.726^{e-07}$), p5 is $7.537^{e-06}$ ($-5.186^{e-05}$, $6.694^{e-05}$), p6 is $-0.002137$ ($-0.009375$, $0.005101$), p7 is $-0.003185$ ($-0.4114, 0.4051$), and p8 =268.6 (261, 276.3), or $$f(x) = p1x^8 + p2x^7 + p3x^6 + p4x^5 + p5x^4 + p6x^3 + p7x^2 + p8x + p9$$

wherein x is a radial distance from a center axis on the fluid path to an inner surface of the tip and coefficients with 95% confidence bounds in parentheses comprise: p1 is 2.285 (1.388, 3.182), p2 is 3.465 (1.782, 5.149), p3 is −15.68 (−20.04, −11.32); p4 is −20.38 (−27.24, −13.52); p5 is 44.27 (36.5, 52.04); p6 is 53.96 (45.69, 62.23); p7 is −58.72 (−64.02, −53.42), p8 is −123.5 (−126.4, −120.6), and p9 is 186.5 (185.6, 187.4).

2. The tip assembly according to claim 1, wherein the tip assembly is characterized in that it is at least selected from: disposable, modular, reusable, transparent, and translucent.

3. The tip assembly according to claim 1, wherein at least one of the attachment portion, the channel portion, and the constriction portion comprises a substance selected from the group of: a glass, a metal, a plastic, a polymer, a nano-based composition, and a composite material comprising at least two different types of substances.

4. The tip assembly according to claim 1, wherein an inner diameter or outer diameter of the attachment portion of the tip assembly fits the flow device in a male to female arrangement respectively.

5. The tip assembly according to claim 1, wherein the channel portion cross sectional area or the constriction portion cross sectional area is bounded by a circle, an ellipse, a rectangle or a square, and wherein the distal end of the constriction portion comprises an inner diameter that is less than or substantially equal to an inner diameter of the opening.

6. The tip assembly according to claim 1, wherein the tip assembly contains a volume which is: about 2 microliters (μl), about 20 μl, about 50 μl, about 200 μl, about 400μl, about 500 μl, about 1 milliliter (ml), about 5 ml, and about 10 ml, and wherein the channel portion inner diameter is about 1.0 millimeter (mm) to about 10.0 mm, and the diameter of the constriction inner diameter is about 0.05 mm to about 2.0 mm, wherein the constriction inner diameter is smaller than the channel portion inner diameter.

7. The tip assembly according to claim 1, further comprising a shoulder extending laterally from of an outward surface of the attachment portion, and a lower ejector section of the flow device is operative to remove the tip assembly from the flow device.

* * * * *

UNITED STATES PATENT AND TRADEMARK OFFICE
CERTIFICATE OF CORRECTION

| | | |
|---|---|---|
| PATENT NO. | : 9,017,991 B2 | Page 1 of 1 |
| APPLICATION NO. | : 13/231592 | |
| DATED | : April 28, 2015 | |
| INVENTOR(S) | : Diefenbach | |

It is certified that error appears in the above-identified patent and that said Letters Patent is hereby corrected as shown below:

IN THE SPECIFICATION

Column 1, line 20, between the "Technical Field" paragraph and the "Background" paragraph insert --This invention was made with government support under grant NS034699 awarded by the National Institutes of Health. The government has certain rights in the invention.--

Signed and Sealed this
Tenth Day of May, 2016

Michelle K. Lee
*Director of the United States Patent and Trademark Office*